United States Patent
Hernandez et al.

(10) Patent No.: US 11,538,571 B1
(45) Date of Patent: Dec. 27, 2022

(54) VIRTUAL WORKLIST FOR ANALYZING MEDICAL IMAGES

(71) Applicant: Compressus, Inc., Austin, TX (US)

(72) Inventors: Albert Hernandez, Tustin, CA (US); Simon Liao, Chino Hills, CA (US); Raymundo Anaya, Corona, CA (US); Laszlo R. Gasztonyi, Fairfax Station, VA (US); Ronald G. Gesell, Stone Mountain, GA (US); Bernadette Baclig, Fullerton, CA (US); Joel Rosenfield, Oceanside, NY (US)

(73) Assignee: Compressus, Inc., Austin, TX (US)

( * ) Notice: Subject to any disclaimer, the term of this patent is extended or adjusted under 35 U.S.C. 154(b) by 100 days.

(21) Appl. No.: 16/221,248

(22) Filed: Dec. 14, 2018

Related U.S. Application Data

(63) Continuation of application No. 11/944,531, filed on Nov. 23, 2007, now Pat. No. 10,169,533.

(60) Provisional application No. 60/867,147, filed on Nov. 24, 2006.

(51) Int. Cl.
*G16H 30/20* (2018.01)
*G16H 10/60* (2018.01)
*G16Z 99/00* (2019.01)

(52) U.S. Cl.
CPC .............. *G16H 30/20* (2018.01); *G16H 10/60* (2018.01); *G16Z 99/00* (2019.02)

(58) Field of Classification Search
CPC .................................. G06Q 50/22–26
See application file for complete search history.

(56) References Cited

U.S. PATENT DOCUMENTS

| | | | |
|---|---|---|---|
| 2003/0100024 A1* | 5/2003 | Cassells | G01N 15/1475 435/40.5 |
| 2006/0168338 A1* | 7/2006 | Bruegl | G16H 40/67 709/240 |
| 2006/0212317 A1* | 9/2006 | Hahn | G16H 40/20 382/128 |
| 2006/0242144 A1* | 10/2006 | Esham | G16H 30/40 |
| 2007/0016686 A1* | 1/2007 | Hollebeek | G16H 30/20 709/238 |
| 2007/0022086 A1* | 1/2007 | Elsholz | G16H 40/63 |
| 2007/0157203 A1* | 7/2007 | Lim | H04L 63/20 718/100 |

OTHER PUBLICATIONS

Leof et al., "New DICOM Extension "General Purpose Worklist" Levels Playing Field" DICOM News https://otechimg.com/publications/html/05-05-4.htm OTech News, vol. 5 iss. 5, Nov. 2000 (Year: 2000).*

DICOM Standard, "Supplement 52: General Purpose Worklist" Version: Letter Ballot Text, Nov. 2, 2000 (Year: 2000).*

(Continued)

*Primary Examiner* — Neal Sereboff

(57) ABSTRACT

Methods and systems for automating and managing efficient workflow for the viewing and analysis of diagnostic images within a healthcare enterprise network generate virtual worklists listing of healthcare data orders allocated to a specific destination. The methods and systems can provide flexible worklist viewing, system administration, and maximized diagnostic throughput.

18 Claims, 31 Drawing Sheets

(56) References Cited

OTHER PUBLICATIONS

Oracle, "File and Record Locking" https://docs.oracle.com/cd/E19455-01/806-4750/6jdqdflt4/index.html (Year: 2010).*
Definition "provide" as downloaded from dictionary.com (Year: 2022).*
Definition "provide" as downloaded from merriam-webster.com (Year: 2022).*
Definition "provide" as downloaded from macmillandictionary.com (Year: 2022).*
Notice of Allowance dated Aug. 23, 2018, mailed in U.S. Appl. No. 11/944,531, pp. 1-15.
Request for Continued Examination (RCE) and RCE Submission, as filed in U.S. Appl. No. 11/944,531, filed Nov. 11, 2017, pp. 1-26.
Final Office Action dated May 12, 2017, mailed in U.S. Appl. No. 11/944,531, pp. 1-36.
Response to Non-Final Office Action dated Sep. 23, 2016, as filed in U.S. Appl. No. 11/944,531, filed Mar. 23, 2017, pp. 1-22.
Non-Final Office Action dated Sep. 23, 2016, mailed in U.S. Appl. No. 11/944,531, pp. 1-38.
Request for Continued Examination (RCE) and RCE Submission, as filed in U.S. Appl. No. 11/944,531, filed Apr. 21, 2016, pp. 1-25.
Advisory Action dated Apr. 4, 2016, mailed in U.S. Appl. No. 11/944,531, pp. 1-3.
Response to Final Office Action dated Oct. 21, 2015, as filed in U.S. Appl. No. 11/944,531, filed Mar. 21, 2016, pp. 1-21.
Final Office Action dated Oct. 21, 2015, mailed in U.S. Appl. No. 11/944,531, pp. 1-36.
Response to Non-Final Office Action dated Jan. 12, 2015, as filed in U.S. Appl. No. 11/944,531, filed Jul. 10, 2015, pp. 1-28.
Non-Final Office Action dated Jan. 12, 2015, mailed in U.S. Appl. No. 11/944,531, pp. 1-34.
Request for Continued Examination (RCE), as filed in U.S. Appl. No. 11/944,531, filed Sep. 8, 2014, pp. 1-2.
Advisory Action dated Aug. 21, 2014, mailed in U.S. Appl. No. 11/944,531, pp. 1-3.
Response to Final Office Action dated May 8, 2014, as filed in U.S. Appl. No. 11/944,531, filed Aug. 7, 2014, pp. 1-18.
Final Office Action dated May 8, 2014, mailed in U.S. Appl. No. 11/944,531, pp. 1-34.
Response to Non-Final Office Action dated Sep. 26, 2013, as filed in U.S. Appl. No. 11/944,531, filed Jan. 27, 2014, pp. 1-18.
Non-Final Office Action dated Sep. 26, 2013, mailed in U.S. Appl. No. 11/944,531, pp. 1-31.
Request for Continued Examination (RCE) and RCE Submission, as filed in U.S. Appl. No. 11/944,531, filed Jun. 18, 2012, pp. 1-15.
Final Office Action dated Dec. 30, 2011, mailed in U.S. Appl. No. 11/944,531, pp. 1-32.
Reply to Non-Final Office Action dated Jul. 26, 2011, as filed in U.S. Appl. No. 11/944,531, filed Nov. 11, 2011, pp. 1-17.
Non-Final Office Action dated Jul. 26, 2011, mailed in U.S. Appl. No. 11/944,531, pp. 1-32.

* cited by examiner

Fig. 3a

MSH|^~\&|||MEDINFORMATIX|OCO_MI|20061123005314+0000||ORU^R01|10|P|
PID|1||3836||PERRY^NATALIE||19780823000000+0000|M|
OBR||122||MR NEURO^MR Neuro Imaging
|||20051026000000+0000|||||||||20061123000000+0000|||C|||||baclig|
OBX|||||CPT Code: 73564  CPT Description: X-Ray, Knee, complete, including oblique, and tunnel, and/or patellar and/or standing view (73564).  History: History  Findings: est  Impressions: est  |||||C|||20051026000000+0000|/^baclig|

Fig. 3b

```
<?xml version="1.0" ?>
<Patient_Report>
    <Checksum>7e189e9ab31e237e84ec5be2b5ded65a</Checksum>
    <ReportStyle>None</ReportStyle>
    <Radiologist>baclig</Radiologist>
    <PatientName>PERRY, NATALIE</PatientName>
    <PatientID>3836</PatientID>
    <StudyUID>1.2.840.113970.3.13.1.1078506.17216057.20051026.1210034</StudyUID>
    <AccessionNumber>1008</AccessionNumber>
    <InstitutionName>SouthWest Clinic</InstitutionName>
    <PatientAge>027Y</PatientAge>
    <PatientSex>M</PatientSex>
    <PatientDOB>8/23/1978</PatientDOB>
    <Requester>Wang</Requester>
    <ServiceDate>10/26/2005</ServiceDate>
    <AccountNumber>3836</AccountNumber>
    <RadiologyNumber>Unknown</RadiologyNumber>
    <CPTCode>73564</CPTCode>
    <CPTDesc>X-Ray, knee, including oblique, & tunnel, & patellar & standing view
</CPTDesc>
    <ExamType>test</ExamType>
    <Technique>test</Technique>
    <ICDCode>959.7</ICDCode>
    <ICDDesc>Other and unspecified injury to knee, leg, ankle, and foot (959.7).</ICDDesc>
    <History>History</History>
    <Findings>est</Findings>
    <Impressions>est</Impressions>
    <DateReviewed>11/23/2006 12:49:53 AM</DateReviewed>
    <CreatedBy>baclig</CreatedBy>
    <DateCreated>11/23/2006 12:49:53 AM</DateCreated>
    <DateSigned>11/23/2006 12:49:58 AM</DateSigned>
    <DateSubmitted>11/23/2006 12:49:58 AM</DateSubmitted>
```

MEDxConnect

Username: wilson  Workstation: joshua

Virtual Worklist

Logout

| | Priority | Notes | Patient ID | Patient Name | Study ID | Institution | Description | Mod | Referring Physician | Study Date/Time | Series Count | Image Count |
|---|---|---|---|---|---|---|---|---|---|---|---|---|
| Claim | Routine | | AN0001 | GORDON HASTE | 734 | Southwest Clinic | CT CHEST FOR PE | CT | Washington | May 21, 2007 11:47 AM | 5 | 320 |
| Claim | Routine | | AN0013 | BECKER TIM | 1.2.840.028059469 | Southwest Clinic | TCI | US | Danson | May 19, 2007 2:54 PM | 1 | 3 |
| Claim | Routine | ⚠ | AN0008 | GEORGIA PEACHES | 2104070521221128 | Baptist Hospital | XR CHEST 2 VW | CR | Gooding | May 21, 2007 12:52 PM | 1 | 3 |
| Claim | Routine | | AN0016 | BROOKS GINGER | 2710 | Southwest Clinic | PELVIC FX ACETABULUM | OT | Hannah | May 17, 2007 2:59 PM | 1 | 3 |
| Claim | Routine | | AN0005 | JULIE WYSCOFF | 2104070516218646 | Southwest Clinic | XR SHOULDER LEFT | CR | Washington | May 21, 2007 9:52 AM | 1 | 3 |
| Claim | Routine | ⚠ | AN0014 | GELLAR RACHEL | 1.2.840.02886131 | Southwest Clinic | OB/GYN | US | Danson | May 11, 2007 2:49 PM | 1 | 7 |
| Claim | Routine | | AN0011 | ARNOLDS PHEBE | 2104061219134C1 | Advanced Imaging | CHEST PA | CR | Walter | May 22, 2007 11:20 AM | 1 | 2 |
| Claim | Routine | | AN0007 | BILLY DAY | 2104070521222100 | Baptist Hospital | XR CHEST 2 VIEWS | CR | Townsend | May 21, 2007 10:20 AM | 1 | 1 |
| Claim | Routine | | AN0015 | NICKS RALPH | 1.2.840.02868130 | Southwest Clinic | PROSTATE | US | Danson | Mar 16, 2007 2:47 PM | 1 | 12 |

Refresh Worklist

Workflow Routing Table

| Field | Type | Description |
|---|---|---|
| RouteID | int | Unique identifier |
| RouteName | varchar(65) | Unique workflow route name |
| Enabled | tinyint(1) | Possible values: (default 1)<br>• 0 – indicates disabled<br>• 1 – indicates enabled |
| ProcedureReason | varchar(65) | Regular expression (default '') |
| FacilityID | int | Ptr to facility in Facilities table (default 0) |
| TimeBased | varchar(16) | Possible values: (default 'None')<br>• None<br>• Period<br>• Daily<br>• Weekly<br>• Monthly |
| StartDate | int(11) | Format YYYYMMDD (default 0) |
| StopDate | int(11) | Format YYYYMMDD (default 0) |
| TimeType | tinyint(1) | Possible values: (default 0)<br>• 0 – indicates All Day<br>• 1 – indicates Start/Stop Time specified |
| StartTime | double | Time in total seconds (default 0)<br>(hours * 3600) + (minutes * 60) + seconds |
| StopTime | double | Time in total seconds (default 0)<br>(hours * 3600) + (minutes * 60) + seconds |
| DayOfWeek | tinyint(1) | Mask for days of the week: (default 0)<br>• 0 bit – no days selected<br>• 1 bit – Monday<br>• 2 bit – Tuesday<br>• 3 bit – Wednesday<br>• 4 bit – Thursday<br>• 5 bit – Friday<br>• 6 bit – Saturday<br>• 7 bit – Sunday |
| FromDay | tinyint(1) | Day of the month (default 0) |
| ToDay | tinyint(1) | Day of the month (default 0) |
| PrefetchStudies | tinyint(1) | Possible values: (default 0)<br>• 0 – do not prefetch studies<br>• 1 – prefetch studies |
| PrefetchReports | tinyint(1) | Possible values: (default 0)<br>• 0 – do not prefetch reports<br>• 1 – prefetch reports |
| PrefetchRouteName | varchar(65) | |

Fig. 6b

Workflow Routes Destination Table

| Field | Type | Description |
|---|---|---|
| ID | int | Unique identifier |
| RouteName | varchar(65) | Unique workflow route name |
| DestType | tinyint(1) | Possible values: (default 0)<br>• 1 – indicates host destination<br>• 2 – indicates group |
| DestinationID | int | Ptr to host in ApplicationEntity table (default 0) |
| GroupID | int | Ptr to group in Groups table (default 0) |

Fig. 6c

Workflow Rules Table

| Field | Type | Null | Key | Default | Extra |
|---|---|---|---|---|---|
| RuleID | int(5) unsigned | | PRI | NULL | auto_increment |
| Name | varchar(30) | | | | |
| TriggerType | int(5) | | | 0 | |
| Enabled | tinyint(1) | YES | | 1 | |
| Rule | text | | | | |
| Comment | varchar(255) | YES | | NULL | |
| SourceAETitle | varchar(65) | YES | | | |
| Modality | text | | | | |
| TimeBased | varchar(16) | | | None | |
| StartDate | int(11) | | | 0 | |
| StopDate | int(11) | | | 0 | |
| CheckDateType | varchar(16) | | | ReceiveDate | |
| TimeType | varchar(8) | | | AllDay | |
| StartTime | double | | | 0 | |
| StopTime | double | | | 0 | |
| DayOfWeek | int(1) unsigned | | | 0 | |
| FromDay | int(1) unsigned | | | 0 | |
| ToDay | int(1) unsigned | | | 0 | |
| ApplyInterval | double | | | -1 | |
| LastRunTime | double | | | 0 | |
| UserId | int(5) | | | -1 | |

Fig. 6d

Sent Images Table

| Field | Type | Null | Key | Default | Extra |
|---|---|---|---|---|---|
| ID | int(5) unsigned | | PRI | NULL | auto_increment |
| FromAETitle | varchar(50) | | | | |
| ToAETitle | varchar(50) | | | | |
| State | varchar(20) | | | | |
| PatientID | varchar(64) | | | | |
| StudyUID | varchar(64) | | | | |
| SeriesUID | varchar(64) | | | | |
| SOPInstanceUID | varchar(64) | | | | |
| Path | varchar(255) | | | | |
| Transfer | varchar(50) | | | | |
| StartTime | double | | | 0 | |
| CompleteTime | double | | | 0 | |
| RetryCount | int(5) | | | 0 | |

Fig. 6e

Received Images Table

| Field | Type | Null | Key | Default |
|---|---|---|---|---|
| ID | int(16) unsigned | | PRI | NULL |
| State | int(5) | | | 0 |
| WorklistState | int(5) | | | 0 |
| PatientID | varchar(64) | | | |
| StuInsUID | varchar(64) | | | |
| SOPInsUID | varchar(64) | | | |
| Path | varchar(255) | | | |
| Transfer | varchar(50) | | | |
| FromAETitle | varchar(50) | | | |
| ToAETitle | varchar(50) | | | |
| DestAETitle | varchar(50) | | | |
| ReceivedTS | timestamp | YES | | CURRENT_TIMESTAMP |

Fig. 6f

Accession Destination Table
- Created after workflow order is filed to keep track of image routing.

| Field | Type | Description |
|---|---|---|
| ID | int(5) | Unique ID |
| AccessionNo | varchar(65) | Accession number |
| DestType | tinyint(1) | ? |
| DestinationID | int(11) | static route |
| GroupID | int(11) | Dynamic route to a group |
| RouteName | varchar(65) | Name |
| FirstSentTS | timestamp | timestamp of first image or report sent |
| LastSentTS | timestamp | timestamp of last image or report sent |

Fig. 6g

PrefetchRoutes Table
- Keeps track of where images should be prefetched from.

| Field | Type | Description |
|---|---|---|
| RouteID | Int(5) | Unique ID |
| RouteName | varchar(64) | Unique route name |
| FromAETitle | varchar(64) | Triggering AET locally for non-workflow rules |
| RemoteAETitle | varchar(64) | Our Prefetch AET listed on remote machine |
| DestinationID | Int(11) | Host ID for remote server we are prefetching from |
| LocalArchiveID | Int(11) | ArchiveID for local machine if it is a local prefetch |
| Days | Int(11) | Number of days old for historical studies |
| SearchBy | Tinyint(1) | 0 for PatientID, 1 for PatName + DOB |
| Enabled | Tinyint(1) | Rule enabled or not |
| PrefetchModel | Varchar(11) | Either Workflow or Simple |
| WorkflowRouteID | int(11) | -1 for non-Workflow prefetch route, otherwise give the routeID listed in WorkflowRoutes |

Fig. 6h

PrefetchPkg Table
- Table used to keep track of historical studies received for prefetching.

| AccesionNo | varchar(65) | Links historical to current study |
|---|---|---|
| StuInsUID | varchar(65) | StuInsUID for each historical study |
| NumOfImages | int(16) | Num of images in historical study |
| NumReceived | int(16) | Num of images received |
| Status | varchar(11) | Pending, Fetched, or incomplete |

Fig. 6i

RecPkg Table
- Keeps track of when a study's first and last images are received by M3

| Field | Type | Description |
|---|---|---|
| RcvdStudyID | int | Unique identifier |
| StudyUID | String | Study Instance UID (DICOM) |
| ArchiveID | int | Pointer to the Archives table. Identifies which archive the study belongs to |
| RcvdStatusID | int | Pointer to an entry in the RcvdStudyStatuses table |
| FirstImageDate | int | First received image date |
| FirstImageTime | float | First received image time |
| LastImageDate | int | Last received image date |
| LastImageTime | float | Last received image time |

Fig. 6j

RcvdStudyStatuses Table
- Defines the possible values for the RcvdStudyStatusID column in the ReceivedStatus table

| Field | Type | Description |
|---|---|---|
| ID | int | Unique identifier |
| Status | String | Possible values:<br>- Receiving<br>- Completed<br>- Incomplete |
| Description | String | Description of status |

Fig. 8b

```
WHILE (1)
{
    GET A LIST OF THE LATEST ENABLED RULES FROM THE ROUTINGRULES TABLE
    GET A LIST OF THE NEW IMAGES IN THE RECEIVEDIMAGES TABLE
    GET THE FIRST NEW IMAGE FROM THE NEW IMAGE LIST
    WHILE NEW IMAGE <> NONE
    {
        PRINT THE NEW IMAGE INFO TO THE LOG FILE
        USE STUINSUID TO QUERY THE WORKFLOWPACKAGE TABLE FOR THE ACCESSIONNO
        IF AN ACCESSIONNO EXISTS (NEW IMAGE IS A WORKFLOW IMAGE)
            IF DESTAETITLE = PREFETCH
                FORWARD WORKFLOW PREFETCH
            ELSE
                FORWARD WORKFLOW IMAGE
        ELSE
            APPLY STUDY ROUTING RULES TO NEW IMAGE
            IF DESTAETITLE = PREFETCH
                FORWARDPREFETCH
            ELSE
                CHECKPREFETCHROUTES
        UPDATE THE IMAGE STATE IN THE RECEIVEDIMAGES TABLE
        GET THE NEXT NEW IMAGE IN THE NEW IMAGE LIST
    }
    SLEEP 15
}

FORWARD WORKFLOW IMAGE:
    USE THE ACCESSIONNO TO QUERY THE WORKFLOW TABLE, CHECK THE STATUS
    IF STATUS = ORDERED
        USE ACCESSIONNO TO QUERY ACCESSIONDEST TABLE FOR DESTLIST AND
            UPDATE FIRSTSENTTS IF THIS IS THE FIRST IMAGE RECEIVED FOR THIS STUDY
        FOR EACH UNIQUE DESTINATION
            (ONLY INCLUDE GROUP DESTINATIONS WITH USERS LOGGED ON)
            ADD NEW IMAGE TO SENTIMAGES TABLE AS QUEUED
    ELSE
        DO NOT ROUTE WORKFLOW IMAGE
```

Fig. 9b

```
MAIN
{
    INITIALIZE ARGVNEW INFO FOR USE WHEN FORKING CHILD DESTINATION PROCESSES
    QUERY SENTIMAGES TABLE FOR ANY "SENDING" IMAGES, UPDATING THEM TO
"QUEUED"
    SET SIGTERM AND SIGCHLD SIGNAL HANDLERS
    OPEN HOSTS TABLE (APPLICATIONENTITY)

WHILE (1)
    {
        GET THE LIST OF HOSTS FROM THE APPLICATIONENTITY TABLE
        PRINT TIMESTAMP EVERY MINUTE
        UPDATEEXECDESTPROC
        SLEEP 10 SECONDS
    }
}

UPDATEEXECDESTPROC:
FOR EACH HOST IN HOSTLIST
    IF CHILD DESTINATION PROCESS ALREADY RUNNING
        CONTINUE;
    FORK/EXECV NEW CHILD DESTINATION PROCESS
    IF MAIN PROCESS
        ADD NEW CHILD DESTINATION PROCESS TO CURRENT CHILD PROCS LIST

IF MAIN PROCESS
    KILL ANY CHILD DESTINATION PROCESSES NO LONGER VALID
    ADD NEW CHILD DESTINATION PROCESSES TO CURRENT CHILD PROCS LIST
```

Fig. 9e

RUNNING AS A CHILD DESTINATION PROCESS:

```
GET OWN PID AND HOSTAETITLE
OPEN SENTIMAGES TABLE
WHILE (1)
{
    GET NEXT QUEUE IMAGE WITH HOSTAETITLE IN SENTIMAGES TABLE
        SET STATE IN SENTIMAGES TO "SENDING"
        FORWARD IMAGE
    GET NEXT RETRY IMAGE WITH HOSTAETITLE IN SENTIMAGES TABLE
        FORWARD IMAGE
    IF NO IMAGES TO ROUTE
        SLEEP 5
}

FORWARD IMAGE:
    GET PORT OF HOSTAETITLE
    ROUTE IMAGE
    CHECK PREFETCH STUDY IMAGE COUNT
    IF COUNT != 0
        SET ISWORKFLOW IMAGE FLAG TO TRUE
    IF RESULT OF ROUTING IMAGE IS SENT
        UPDATE SENTIMAGES STATE TO "SENT"
        IF PREFETCH WORKFLOW IMAGE
            UPDATE SENTSTUDIES TABLE WITH STATE EQUALS
"WORKFLOWPREFETCHSENT"
        ELSE
            GET ACCESSIONNO FROM WORKFLOWPACKAGE TABLE
            IF ACCESSIONNO EXISTS (IS PRIMARY WORKFLOW IMAGE)
                GET ARCHIVEID OF FROMAETITLE
                GET STUDY IMAGE COUNT FROM STUDYLEVEL TABLE
                GET IMAGES SENT COUNT FOR STUDY
                IF STUDY IMAGE COUNT = IMAGES SENT COUNT
                    UPDATE SENTSTUDIES TABLE WITH STATE EQUALS
"WORKFLOWPRIMARYSENT"
        ELSE
            IF RETRY COUNT MAX REACHED
                UPDATE SENTIMAGES STATE TO "FAILED"
                UPDATE SENTSTUDIES TABLE WITH STATE EQUALS "FAILED"
            ELSE
                UPDATE SENTIMAGES STATE TO "RETRYING"
```

VIRTUAL WORKLIST FOR ANALYZING MEDICAL IMAGES

RELATED APPLICATION

This application claims priority of U.S. Provisional Application 60/867,147, entitled "Virtual Worklist For Analyzing Medical Images", filed on Nov. 24, 2006, which is incorporated herein by reference in its entirety. This application is also related to co-pending U.S. patent application Ser. No. 11/944,534 entitled "Pre-fetching Patient Data for Virtual Worklists" and U.S. patent application Ser. No. 11/944,530 entitled "System Management Dashboard", which are being filed concurrently with the present application and is hereby incorporated by reference in its entirety.

FIELD OF THE INVENTION

The present invention relates to methods and systems for automating and managing workflow for image analysis, more particularly managing workflow of medical image analysis studies within an enterprise wide, diagnostic healthcare environment.

BACKGROUND OF THE INVENTION

Presently, healthcare enterprises generally are plagued by the lack of connectivity and interoperability between disparate hospital information systems (HIS) and radiology information systems (RIS) from a variety of vendors. Typical systems may employ a mix of incompatible formats for patient textual records and diagnostic images, such as HL7, DICOM, TIFF, JPEG, IHE, and XML.

The lack of interoperability between existing information and imaging systems is one of the most critical problems facing the diagnostic and management effectiveness of the healthcare profession today. This fundamental problem not only diminishes the potential benefits of medical care capability, it also diminishes the financial bottom line of every healthcare facility. In addition, solving the interoperability problem is essential for eventual implementation of a standard-based enterprise-wide Electronic Health Record.

One of the major goals of the Integrating the Healthcare Enterprise (IHE) is to have the multiple HIS, RIS, PACS, and proprietary systems appear to be a single working virtual entity implemented on one enterprise network. An augmented, interoperative, integrated network provides a basis for achieving this goal of seamless enterprise integration. This is especially true in managing and automatically routing the enterprise workflow in the analysis of diagnostic images.

Typical problems involved in managing workflow of diagnostic images in a healthcare enterprise involve having an imaging specialist or diagnostic physician at the right place and at the right time to analyze diagnostic images. All too often imaging specialists must physically travel from one facility to another, wasting valuable time and increasing overall costs. Even when an enterprise is networked, but not automated, an imaging specialist or diagnostic physician must log on to several HIS/RIS/PACS systems and often manually seek out the needed patient data. In addition, a specialist, such as a neuro-radiologist, at one facility may need to diagnose and report on patients from other facilities. Information for such diagnostic work may require input from several facilities and several HIS/RIS/PACS systems.

Naturally, the incompatibilities of multiple HIS/RIS/PACS systems preclude automatically acquiring, compiling, parsing, routing, sorting, and displaying a network-wide composite list of diagnostic studies to be performed—known as a "worklist". The incompatibilities preclude automatically accessing all relevant diagnostic images, history, reports, and patient records, which are required to process the entries in the worklist at a single workstation. Further, relevant diagnostic images, history, reports, and patient records may exist in diverse formats and reside on diverse network file servers, imaging systems, workstations, and archives. Thus, there is a need for a healthcare enterprise worklist that is custom filtered for a specific healthcare diagnostician. Using this worklist, the diagnostician can log onto a single network workstation at one location with access to all the images, records, and archive reports for each subject of a worklist entry.

SUMMARY

The various embodiments provide methods and systems for automating and managing the workflow of viewing and analyzing images within an enterprise-wide diagnostic healthcare environment. The embodiment methods and systems can provide enterprise-wide workflow load balancing, customized diagnostic workflow routing, information exchange, flexible worklist viewing, system administration, and maximized diagnostic throughput. The embodiment methods and systems can provide a time saving and cost effective solution for achieving an efficient enterprise-wide diagnostic process by providing an administrator with information to work proactively in making a healthcare enterprise efficient and cost effective. Embodiments may support any or all established or emerging standards for information formatting, transmission, and storage and for image compression.

Various embodiments can compile an enterprise-wide Master Worklist composed of zero or more image analysis orders acquired and compiled from multiple, potentially diverse HIS, RIS, PACS, and imaging systems as well as other network workstations which may initiate an order.

The automated management of workflow and routing and the merging of imaging system worklists into an enterprise-wide Master Worklist may be presented to a logged-in diagnostician as a seamless, integrated, continually synchronized system executing on a single platform or on a network of workstations and servers. A system embodying such a method may be a step toward the objectives of the Integration of Healthcare Enterprises (IHE).

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

FIGS. 3a, 3b, and 3c are examples of representations of patient demographic data and other data related to a patient.

FIG. 4a is an example of a Master Virtual Worklist, and FIG. 4b is a sample display of a Filtered Worklist.

FIGS. 5a through 5f illustrate example user interface screens for entering and updating enterprise workflow routes, routing rules, and physician groups.

FIGS. 6a through 6j describe example record formats for various database tables of an embodiment.

FIG. 8a through FIG. 11 are flowcharts and pseudo code which provide detailed examples of workflow routing processing.

DETAILED DESCRIPTION OF THE PREFERRED EMBODIMENTS

Figure 1:
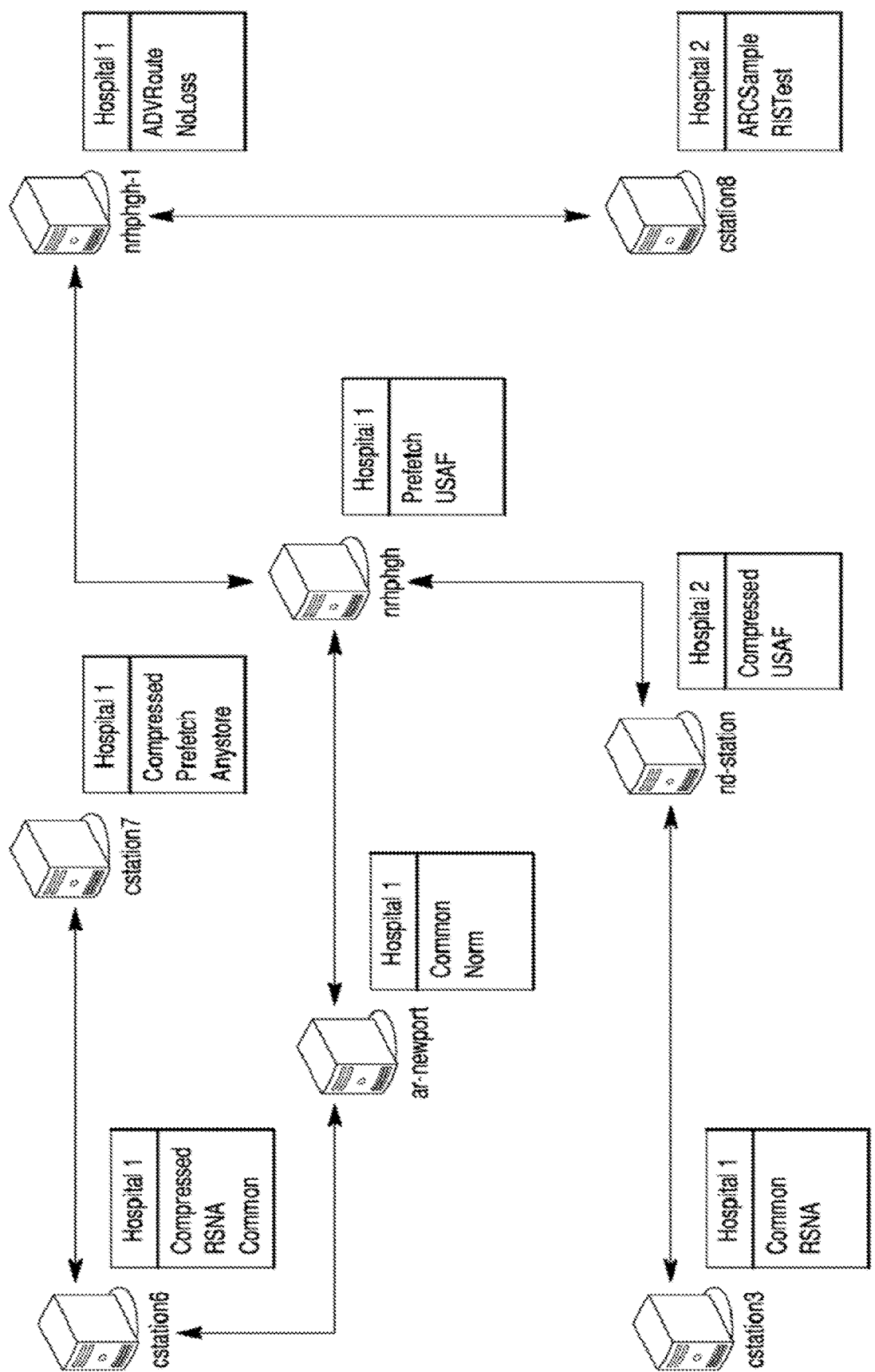
FIG. 1 is a schematic diagram of an example of a small network of workstations and servers linked by any of various hardware and communications protocols.

The various embodiments will be described in detail with reference to the accompanying drawings in the Figures. Wherever possible, the same reference numbers will be used throughout the drawings to refer to the same or like parts.

Efficiency of workflow in a healthcare enterprise is very important to the healthcare delivery system. With doctors and diagnostic equipment in high demand and ever increasing pressures on healthcare institutions to control costs, it is very important to maintain highly efficient workflow across the healthcare enterprise. This is particularly important for the processing of diagnostic images by the imaging specialists and diagnostic physicians with the skills to interpret the images. Such specialists are always in short supply and constant demand. These specialists require detailed images, accurate patient data, and medical records to perform their jobs.

Diagnostic images may be obtained from a large number of different, sophisticated, stand alone diagnostic imagers (e.g., X-ray, CT scanners, PET scanners, MRI scanners), and different labs and examination rooms—each with their own data formats, communication protocols and user interfaces. In particular, image studies using one or more types of medical diagnostic imagers (sometimes referred to herein as "modalities") generate large volumes of image data, with different types of imagers generating different types of image data, all of which must be routed, stored, displayed and managed efficiently by the enterprise system. Image data files are typically quite large in terms of total bytes of data, and thus must be centrally stored and managed (versus redundantly stored on multiple workstations).

To make a diagnosis, the diagnostic physician may require a number of images of different modalities (e.g., X-ray and MRI to diagnose a joint injury, or CT, MRI and PET to diagnose a head injury). Additionally, Patient records and other data are likely stored in other data systems. Thus, presenting the imaging specialist or diagnostic physician with all of the images, patient data, and other data needed to complete a particular diagnostic task presents a complicated network challenge. Providing specialists with single workstation access to all the required data can have a significant impact upon the overall efficiency of a healthcare enterprise. This combination of high complexity in imaging systems, large data file size, endemic hardware/software incompatibilities among imaging systems, high user demands and expectations, and the urgency and criticality of diagnostic services places unique demands on the enterprise system. Thus, there is a need for network system tools that automatically acquire, compile, parse, route, sort, and display an imaging study "worklist," namely a network-wide composite list of pending diagnostic studies.

A "Virtual Worklist" embodiment consists of workflow packages. A workflow package is a consolidated patient folder and may contain all current and historical healthcare records. In addition, the workflow package may contain information such as metadata markers which indicate the virtual path the healthcare data has taken through the healthcare enterprise system. Such metadata markers may indicate the healthcare data source. For example, these metadata markers may indicate which servers and workstations have accessed the healthcare data and the amount of time the healthcare data file spent at various components within the healthcare enterprise system. A workflow package may also be generated to record all relevant information regarding each healthcare data. In this manner, embodiments of the present invention are able to track the healthcare data through out its residence within the healthcare enterprise system.

A Worklist is sometimes referred to as a "virtual worklist" because it is a compiled composite of all image analysis orders on all HIS/RIS systems within the healthcare enterprise network. As used herein, "study order" or simply an "order" refers to an order for analyzing a patient's healthcare data or more specifically patient image study. Each study order in a compiled Master Worklist references a specific patient and the patient's health related data including a specific set of images of the patient which require analysis.

The various embodiments automatically compile the necessary data from across the enterprise system to generate a Master Worklist or virtual worklist of imaging studies within the enterprise. Additionally, an embodiment can generate a custom Filtered Worklist of study orders from the Master Worklist that is specific to a designated group of one or more diagnosticians, physicians, specialists or patients. Any member of the group may then log onto a diagnostic workstation anywhere on the network, claim a study order in the Filtered Worklist (i.e., select the study order for analysis), analyze the study order, and create a report for the study order. Each Filtered Worklist contains only those study orders which a member of the group associated with the Filtered Worklist may claim and subsequently analyze. Filtered Worklists are specific subsets of the Master Worklist and are tailored for each particular physician/diagnostician group by a set of worklist routing rules. A further embodiment makes available all patient demographic information, records, and images associated with each study order claimed by the diagnostician. The patient's images, records, and information also potentially include all enterprise-wide historical studies related to the subject of a claimed study.

The image analysis study orders within a Filtered Worklist correspond to the gathering and routing of the images and other information needed to perform a particular image analysis. The destination of the images and information may be a participating group of physicians or an individual physician. The destination is controlled by a set of customized workflow routing rules programmed by an administrator. The workflow routing rules may be conditionally based upon any combination of the modality of the image (or images), a body part in the image, the referring physician, location of the patient, patient's insurance carrier, and so on. To maximize productivity and reduce workload bottlenecks, diagnosticians may access Filtered Worklists from any workstation within the enterprise network. The Master Worklist further permits proactive management of workflow by balancing the distribution of workflow load among the physicians and physician groups.

The various embodiments can be configured as combinations of hardware and software providing seamless connectivity between all image acquisition, PACS, HIS and RIS systems. An embodiment is built upon an underlying infrastructure of components which work together to enable an interoperable healthcare enterprise system. The underlying infrastructure may be composed of existing computer networks, servers, information systems, imaging systems, workstations, personal computers, and other network nodes in communication with each other. The infrastructure may also include application software executing on the network infrastructure. The software may be distributed among the nodes, such as servers and workstations, and may include client and server software components.

FIG. 1 illustrates a simple example of an interoperable system infrastructure within an enterprise healthcare system. A networked system of workstations, such as illustrated in FIG. 1, may be linked by any of various hardware and communications protocols, such as Ethernet, TCP/IP, Internet, wireless IEEE 802.11, or other established or emerging data communication technologies.

The underlying infrastructure may be augmented with software (and further computer hardware as necessary) in order to solve interoperability problems to form an augmented, integrated "Interoperable Network." Such an integrated Interoperable Network may adhere to and translate between accepted medical data and communications standards including HL7, DICOM, and XML. The Interoperable Network can leverage existing communications infrastructure to interconnect existing information subsystems and applications through standardized and proprietary formats. The Interoperable Network may also provide intelligent auditing of the workflow between subsystems. The Interoperable Network may use the communications protocols and semantics of each participating networked imaging subsystem, information server, and workstation. The Interoperable Network may mediate interoperability between different applications, creating a virtual integrated, enterprise-wide information system that adheres to the IHE technical framework. An Interoperable Network underlies the embodiments described herein.

Routing of images and patient data is most effective when all the enterprise's acquisition devices and information subsystems are integrated and interoperable and can seamlessly exchange information. Software interfaces and modules can unite extant HIS, RIS, PACS, and/or diagnostic workstations to support the interchange and translation of patient records, image analysis studies, images, and reports between otherwise independent systems from various vendors. In particular, DICOM modality worklists provide a well-known interface to the image acquisition devices. The software of the augmented infrastructure can be configured to translate formats between DICOM, HL7, XML, IHE, and other standards. This integration between systems can then allow diagnosticians to read images and create reports wherever they happen to be within the enterprise's network. Software tools currently exist for partly achieving interoperability between vendor specific systems. For example, the Iguana and Chameleon software from iNTERFACEWARE Inc. (Toronto, Canada) can interface RIS and PACS systems using disparate variations of HL7 from multiple vendors on the same enterprise network. Nevertheless, embodiments of the method and system described herein may provide even further integration.

The DICOM modality worklist can be the basis of an enterprise wide solution supported by the Interoperable Network. This permits networked acquisition devices to access any DICOM modality worklist throughout the enterprise network. For example, an acquisition device in one facility can receive the needed patient information that has been compiled from multiple facilities and multiple HIS/RIS/PACS systems. This simplifies the acquisition device workload and speeds up workflow when multiple facilities are involved.

Different systems may use a number of proprietary data formats to store and move information. The underlying Interoperative Network can map the data elements between dissimilar systems so each independent system can securely and appropriately use information from each other. To ensure accurate translation the Interoperable Network system must identify and transfer demographic and other patient record information between the authoritative systems. This information can then be reliably used to manage the location, transfer, reformatting, pre-fetching, distribution, and delivery of new study orders, patient records, new and archived images, archived studies and reports, and newly created reports. An embodiment may support DICOM, HL7, XML, SSL, TLS and other standards to further support HIPAA compliance in both procedural and security areas.

Figure 2A:
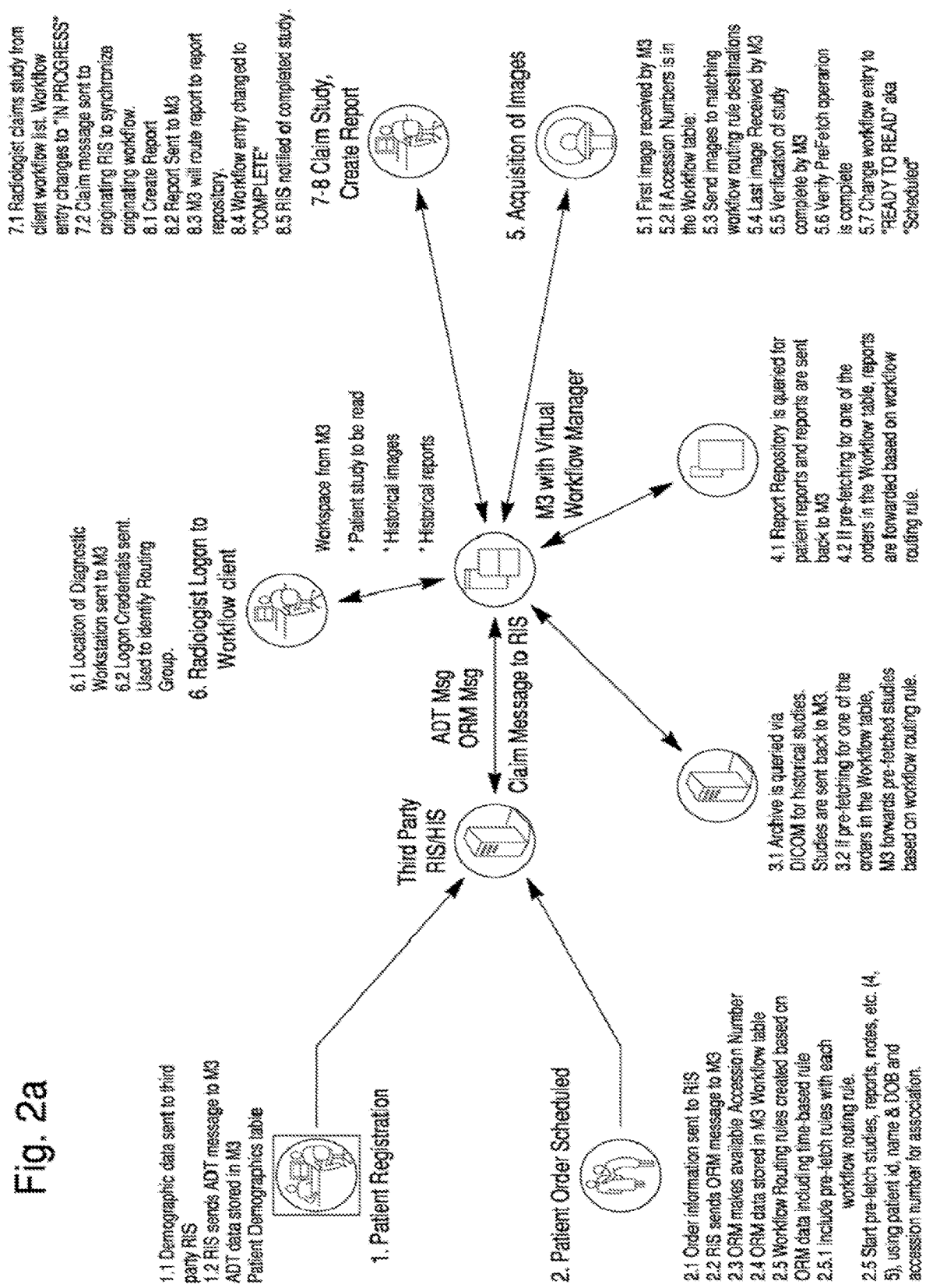
FIGS. 2a and 2b depict example scenarios for the operation of an embodiment.
Figure 2B:
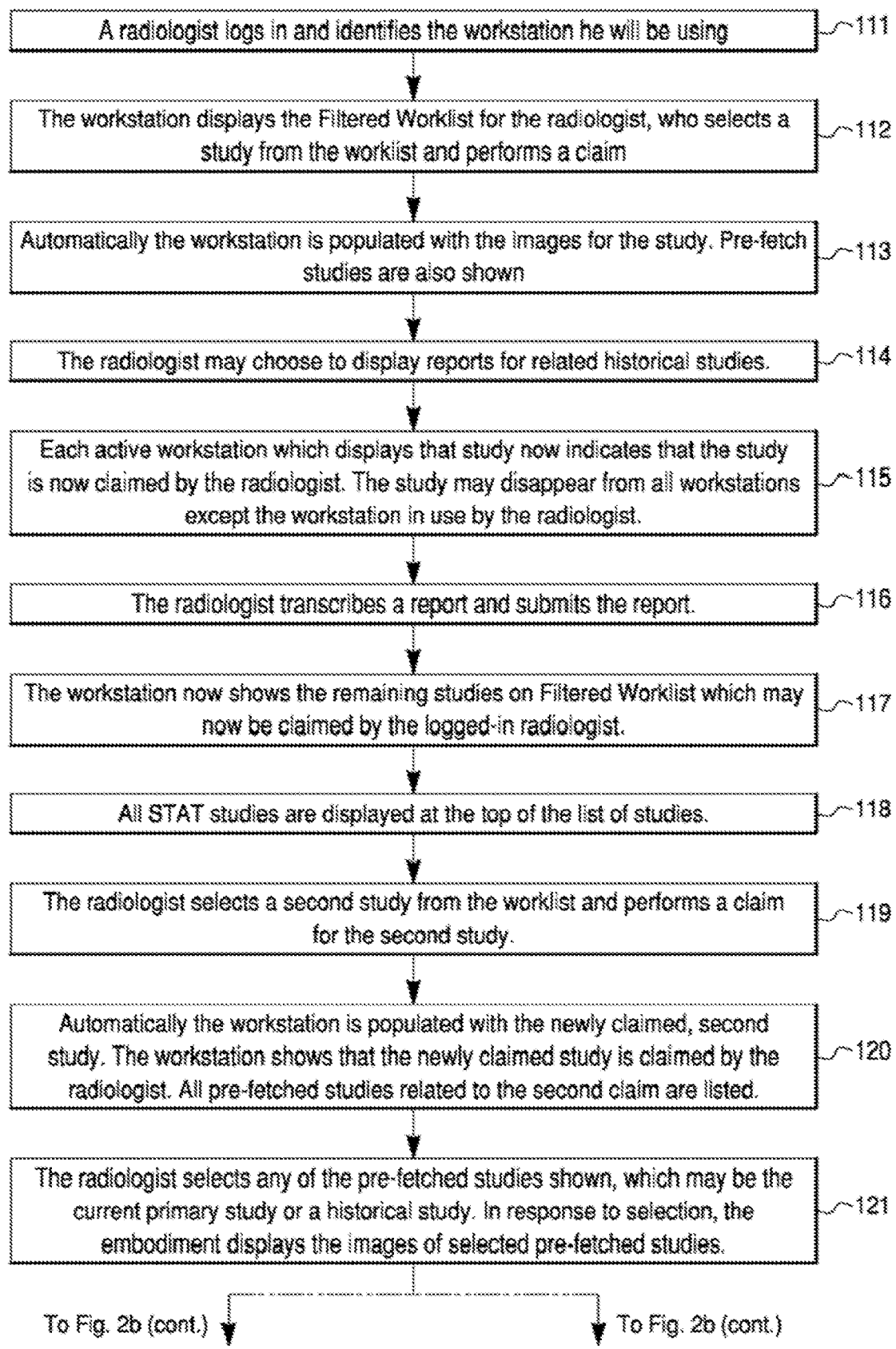
Figure 2B:
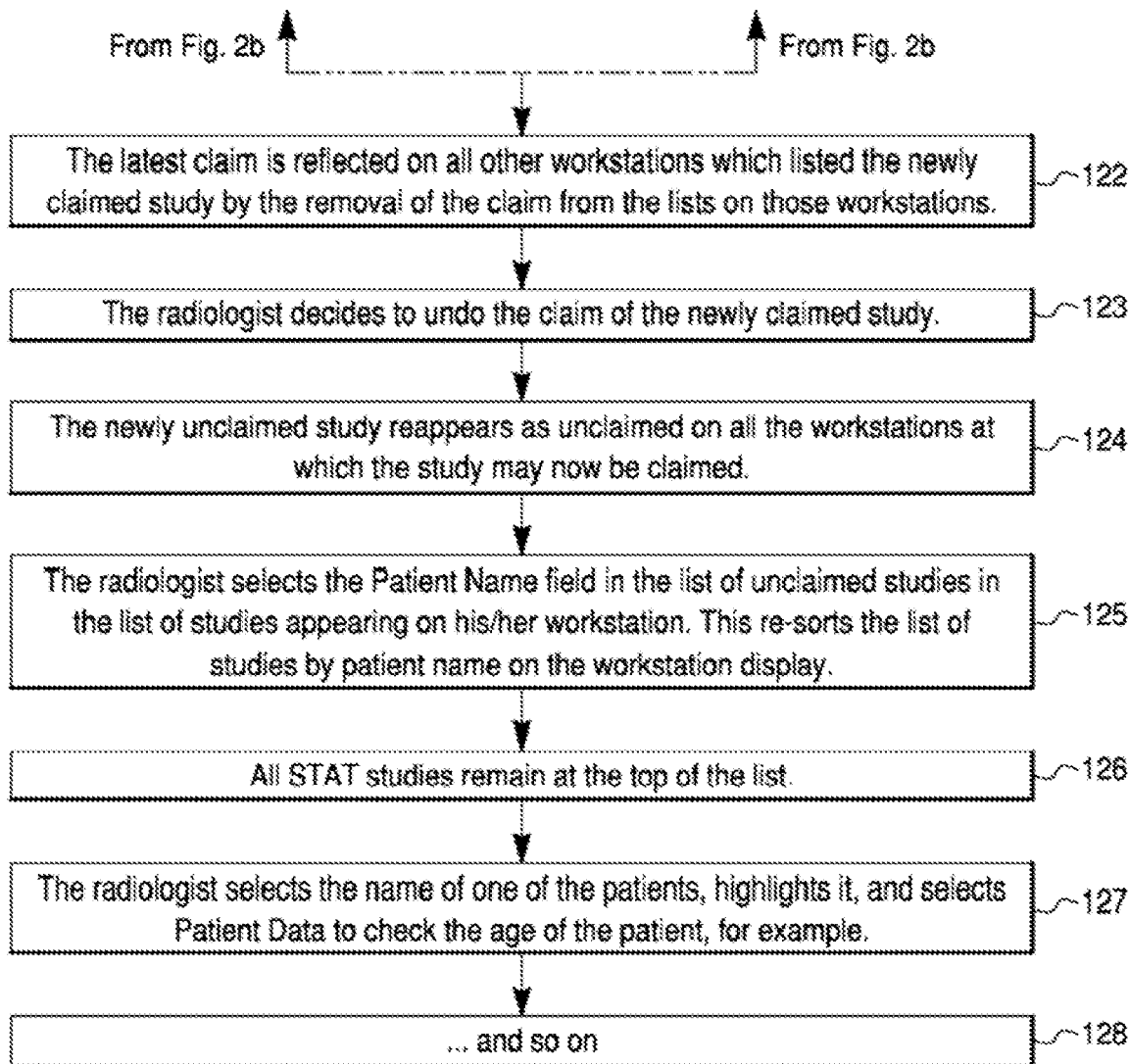

FIG. 2a is a diagram of a network of enterprise workstations. As in FIG. 1, the workstations illustrated in FIG. 2a can be linked by any of various hardware and communications protocols, such as Ethernet, TCP/IP, Internet, wireless IEEE 802.11, or other technologies of the future. FIG. 2a provides an overview of the typical activities which may occur as an embodiment functions. Reference to FIGS. 2a and 2b will be made to give an overall view of the typical operation of an embodiment.

In this description, a "study order" normally refers to a message or data structure containing information about a patient and a requested diagnostic procedure for the patient. A study order (or simply, order) is a request for a primary set of diagnostic images of the patient and for subsequent image analysis to be performed on the images by an imaging specialist or diagnostic physician. A "study" generally refers to a set of images which an order will generate or has generated. The "primary study" is the set of images for which an analysis and report is requested. A "historical study" is generally retrieved from an archive on the network, may have been generated by some previous order, and may have an associated "historical report". Sometimes "study" is loosely used to refer to a study order, the associated primary study, and/or the collection of all historical reports and other information about the patient who is the subject of the study order. An "order" within a displayed worklist of orders succinctly denotes and implicitly references the study images, the historical images and reports, and all other accessible records regarding the patient.

One typical activity of the embodiment exemplified in FIG. 2a may be Patient Registration 1, in which patient demographics and other information are either newly entered or acquired from a network archive (e.g., a database server connected to the network). Another typical activity, Patient Order Scheduled 2, may access the patient demographic data and enter a patient study order through a RIS or HIS system of some third party vendor. The new study order may be in the form of an ORM message to an embodiment of the method or system described herein, such as the Compressus $M^3$ Virtual Workflow Manager (WFM) running on a network server. The study order may be stored in a Master Virtual Workflow list, or simply in a Master Worklist. The Workflow Manager applies custom programmed routing rules to the contents of the study order in the Master Worklist to determine a virtual destination for the study order. The virtual destination of a study order is a defined group of one or more known users, which may be radiologists, specialists, or other physicians.

Storing a new study order in the system may initiate or schedule the pre-fetching of patient-related historical studies, archived images and reports, lab results, notes, and the like which can be archived in databases throughout the network. Pre-fetch Studies 3 and Pre-fetch Reports 4 shown in FIG. 2a illustrate the pre-fetching process according to the rules applied to the studies in the Master Worklist. Pre-fetching can be done by the Workflow Manager, which locates the patient-related extant images, studies, and reports by querying network nodes (archives, imaging systems, workstations, and other nodes). The Workflow Manager then retrieves, transfers, routes, and reformats as necessary the images, studies, reports, and other patient-related information to a programmed, designated destination on the network. The destination may be virtual, such as a dynamic assignment to a named group of diagnosticians.

Acquisition of Images 5 process shown in FIG. 2a acquires, transmits, and reformats as necessary the new images which require analysis. As images, studies, reports, and other data are located, assembled, and transmitted to the determined destinations, the status of this activity is monitored by the Virtual Workflow Manager. When all the historical and current data has been pre-fetched and sent to the destination and when any failed attempts have generated error indications, an image analysis study is ready to be claimed. Some time thereafter, a radiologist (or specialist, diagnostician or physician) may log onto a workstation imitating the Radiologist Logon to Workflow Client 6 process which displays a Filtered Worklist specific to the user. The radiologist claims an image analysis study order, as shown in Claim Study 7 process of FIG. 2a. The radiologist subsequently creates a new image analysis report, as shown in the Create Report 8 process. After the report is completed, the status of the study order in the Master Worklist reflects the completed state, and the Worklist Manager routes the report to a repository destination according to the routing rules. Throughout these processes the Worklist Manager maintains synchronization with any third-party RIS or other image source to reflect the latest status of the study order locally on the RIS.

FIG. 2b illustrates an example sequence of interactions which may occur between a physician and a diagnostic workstation when using an embodiment. FIG. 2b is an expanded example of interactions which may possibly occur in FIG. 2a at Radiologist Logon to Workflow Client Workstation 6, Claim Study 7, and Create Report 8. First, a user, such as a radiologist, logs in onto a diagnostic workstation, step 111. The workstation then displays a Filtered Worklist prepared specifically for the group to which the radiologist belongs. The radiologist selects a study order from the worklist and performs a claim on the selected order, step 112. Automatically, the system populates the user's workstation with patient images, records, primary study images, and pre-fetch studies, step 113. The workstation may present the radiologist with a list of the primary images and the historical images and reports, which the radiologist may choose to display, step 114. All other workstations on which the newly claimed image analysis study order appears may now show that the study order is claimed by the radiologist. Alternatively, the study order may disappear from all other workstations except the workstation being used by the radiologist, step 115. The radiologist creates a report and submits the report, step 116. The workstation then displays a list of the remaining studies which the logged on radiologist (or anyone else in the same group) may now claim, step 117. The workstation may display all STAT claims at the top of the list, step 118. The radiologist may select another (second) study order from the worklist and perform a second claim, step 119. In response, the system automatically populates the workstation with the second claimed study order, step 120. All pre-fetched studies related to the second claim may be displayed on the workstation. The radiologist may select any of the pre-fetched studies shown, which may be the current primary study and/or a historical study. In response to selections, the system displays the images and pre-fetched studies of the selected second claimed study order, step 121. All other workstations which display a worklist including the second study order newly claimed by the radiologist now show that the second claimed study order is claimed. Alternatively, the second, newly claimed study order may disappear from the lists displayed on all the other workstations, step 122. The radiologist may decide to undo the claim on the most recently claimed study order, step 123. The newly unclaimed study order then reappears as unclaimed on all the workstations at which the study order may now be claimed, step 124. The radiologist may select the Patient Name field in the list of unclaimed studies in the list of studies appearing on the workstation. This selection re-sorts the list of studies on the workstation display by patient name, step 125. Nevertheless, all STAT studies may remain at the top of the list, step 126. The radiologist may select the name of one of the patients, highlight it, and select Patient Data to display the age, gender, or other details about the patient, step 127. The radiologist may then perform further interactions with the system such as those listed above, step 128.

One of the most common sources of incorrect information in patient records and studies results from errors made during repeated data entry steps at each application or acquisition device included in the diagnostic process. An embodiment supporting the DICOM standard allows an acquisition modality to retrieve patient demographic data from the health information system. Using the patient demographic data from the original entry reduces errors and helps maintain information integrity, as shown in Patient Registration 1 process of FIG. 2a. Accuracy of data entry is important to automated routing of worklist studies and the related images, because the routing rules examine the data and route studies accordingly. For example, a routing rule may be based on the ordering physician's name, the modality of the study order being ordered, the location of the original imaging device, or even possibly the patient's insurance carrier. Alternative basis for routing rules are possible depending upon the healthcare enterprise administrator's needs or requirements.

FIG. 3a provides an example of a patient record which may contain the information entered during the Patient Registration 1 process shown in FIG. 2a. Alternatively, the patient record may contain information collected from multiple sources throughout the enterprise. In particular, the patient information may be made available to the diagnostician during the process of claiming a study order, as in the Claim Study 7 process of FIG. 2a or process step 127 of FIG. 2b.

In FIG. 3a the patient record data is represented as an HL7 ORM message. In FIG. 3b the patient record data is represented in XML. XML may serve as a more flexible, system-wide, platform independent format for storing patient demographic and other information. The XML formatted information may have been composed by reformatting the patient data from a HL7, RIS, or DICOM source, such as in FIG. 3a. For example, the data may have been initially entered through a workstation which stores the patient information in a vendor-specific version of HL7. Alternatively, XML may be the vendor-specific format employed by an individual data entry workstation. In any case, an embodiment may include software to automatically access, parse, cross-check, translate, and compile data from a variety of differing formats on a number of workstations or servers from different vendors.

Figure 3C:
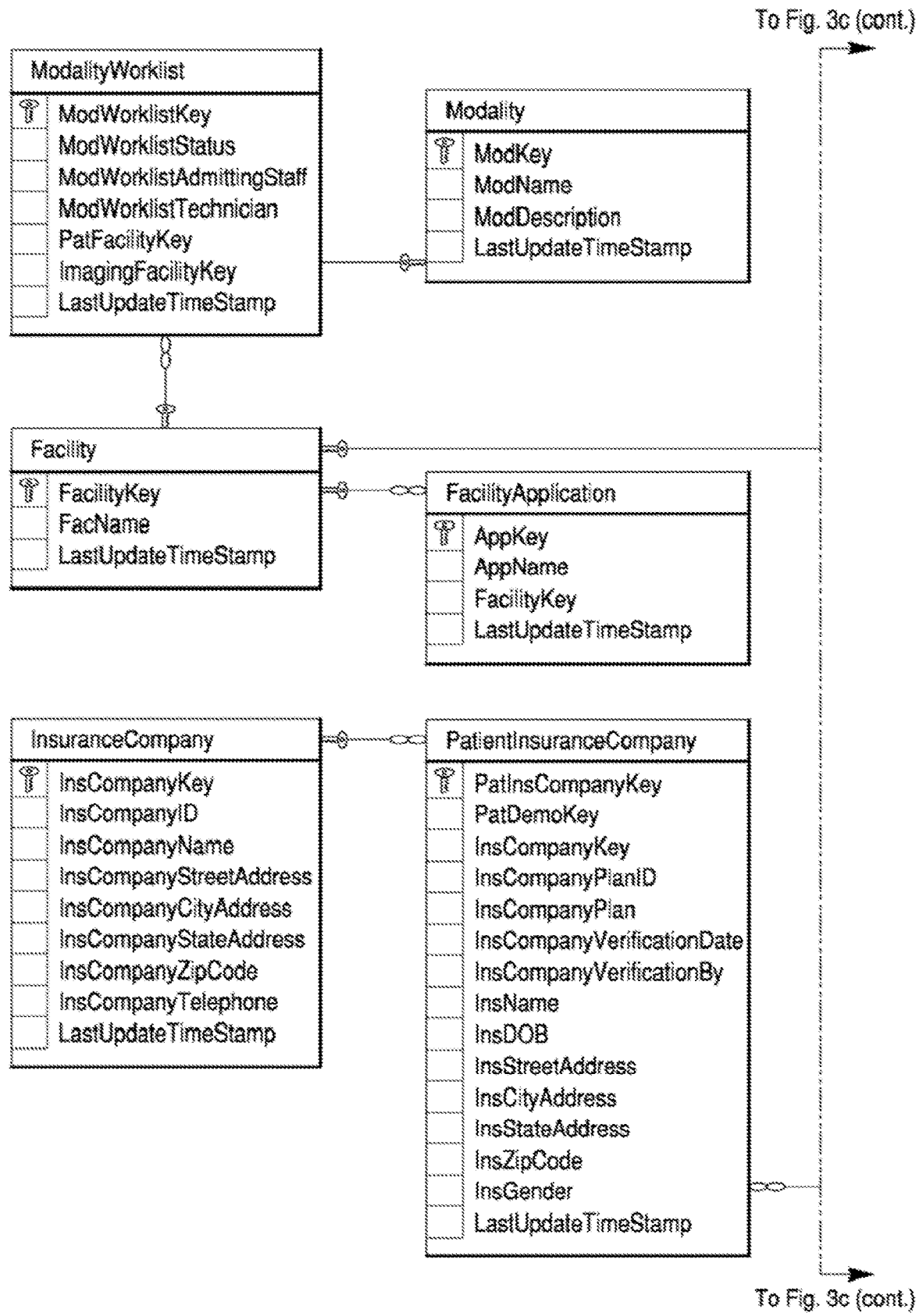
Figure 3C:
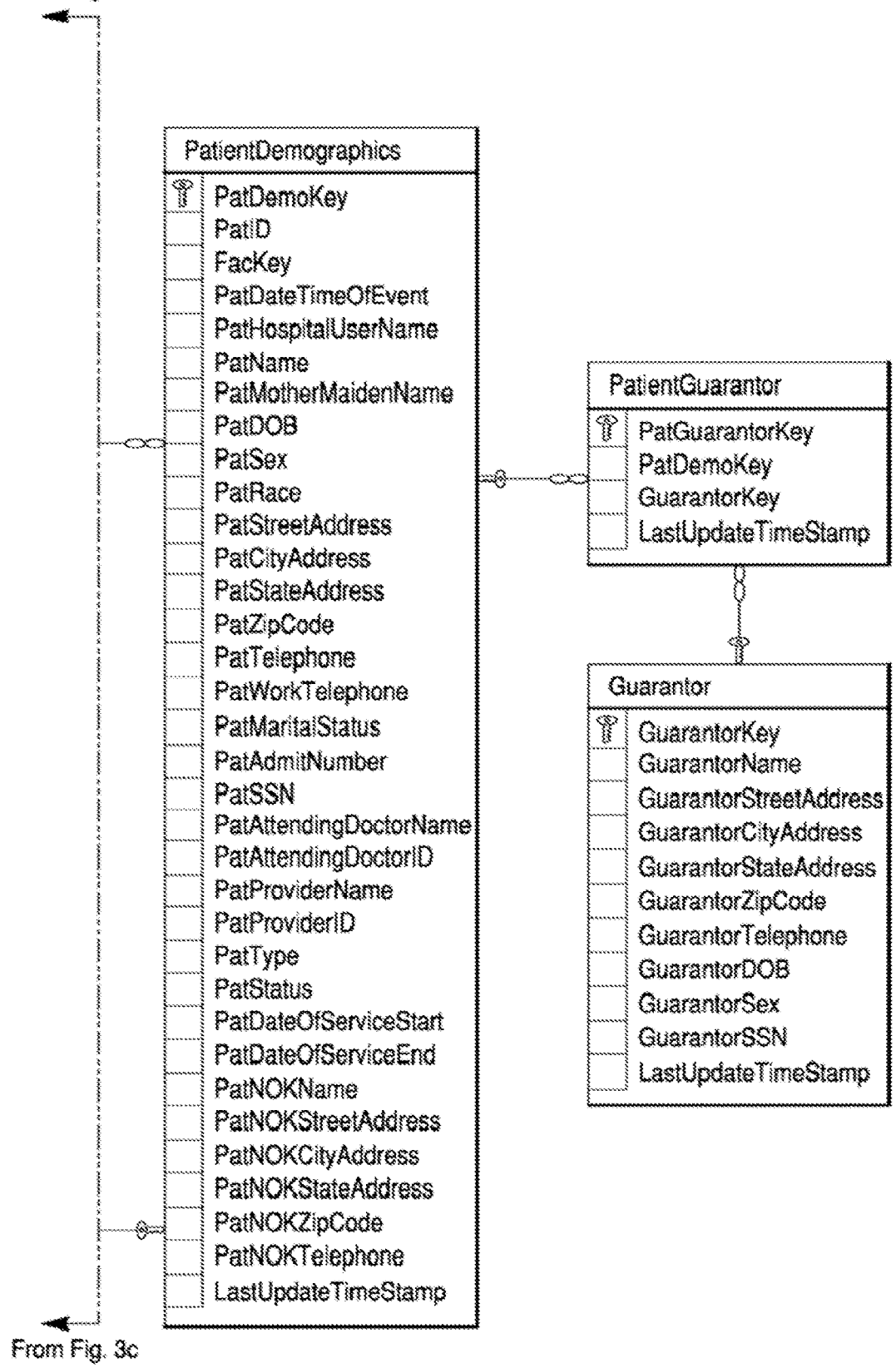

A solution to the problem of numerous incompatible formats may be to collect and organize the network locations of all the demographics and records, current and historic studies, study images, reports, and other data related to a patient in an enterprise-wide database. FIG. 3c is a diagram of related data structures of an embodiment showing relationships among the data structures which may embody the data related to a patient within an enterprise-wide database. The data structures of FIG. 3c may, for example, be used to capture in a computer memory the patient information contained in the examples of FIG. 3a or 3b. Further data structures will subsequently be discussed in connection with the collection of studies and automatic routing of patient information. Some of the data structures may be kept current within a permanent database; other data structures may be generated temporarily by the Workflow Manager. The data structures of FIGS. 3a through 3c relate to the embodiments, because the custom programmed rules provided to the Workflow Manager may test the contents of the various fields of the data structures to determine the destination of a study order in the Master Worklist.

Figure 4A:
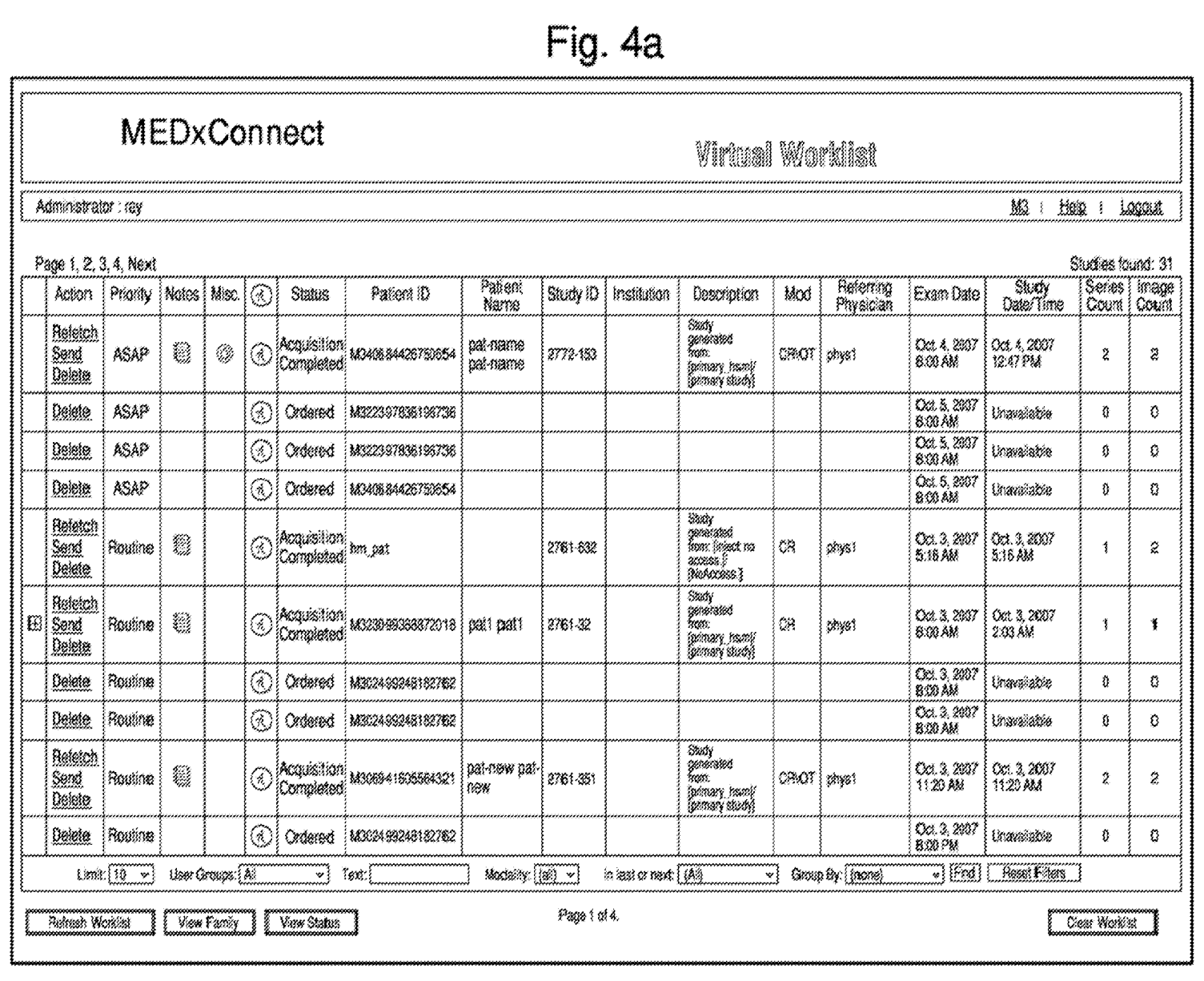

FIG. 4a shows an example of the study orders which may populate the virtual Master Worklist. These constitute the compilation of all studies originating from throughout the Interoperable Network of the healthcare enterprise. A third-party HIS or RIS may typically originate a study order by sending an ORM message, such as shown in FIG. 3a, to the Workflow Manager which enters the new study order in the Master Worklist. The Workflow Manager determines the destination group of the new study order by applying custom programmed routing rules to the contents of the new study order. The Workflow Manager then creates a Filtered Worklist for each destination group. FIG. 4b shows a sample Filtered Worklist. The Filtered Worklist contains only those study orders from the Master Worklist which a member of the corresponding destination group may analyze.

Figure 5A:
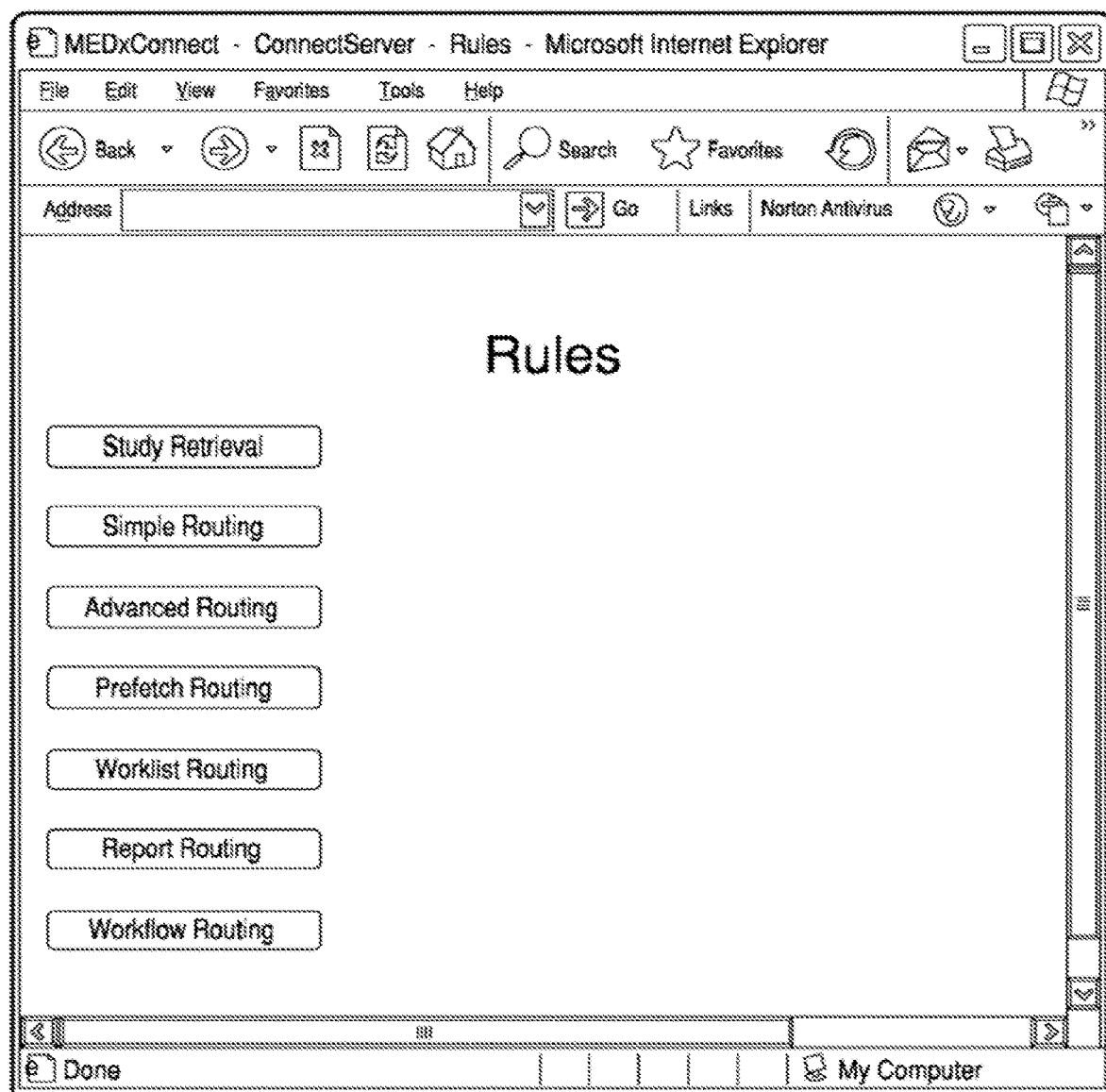
Figure 5B:
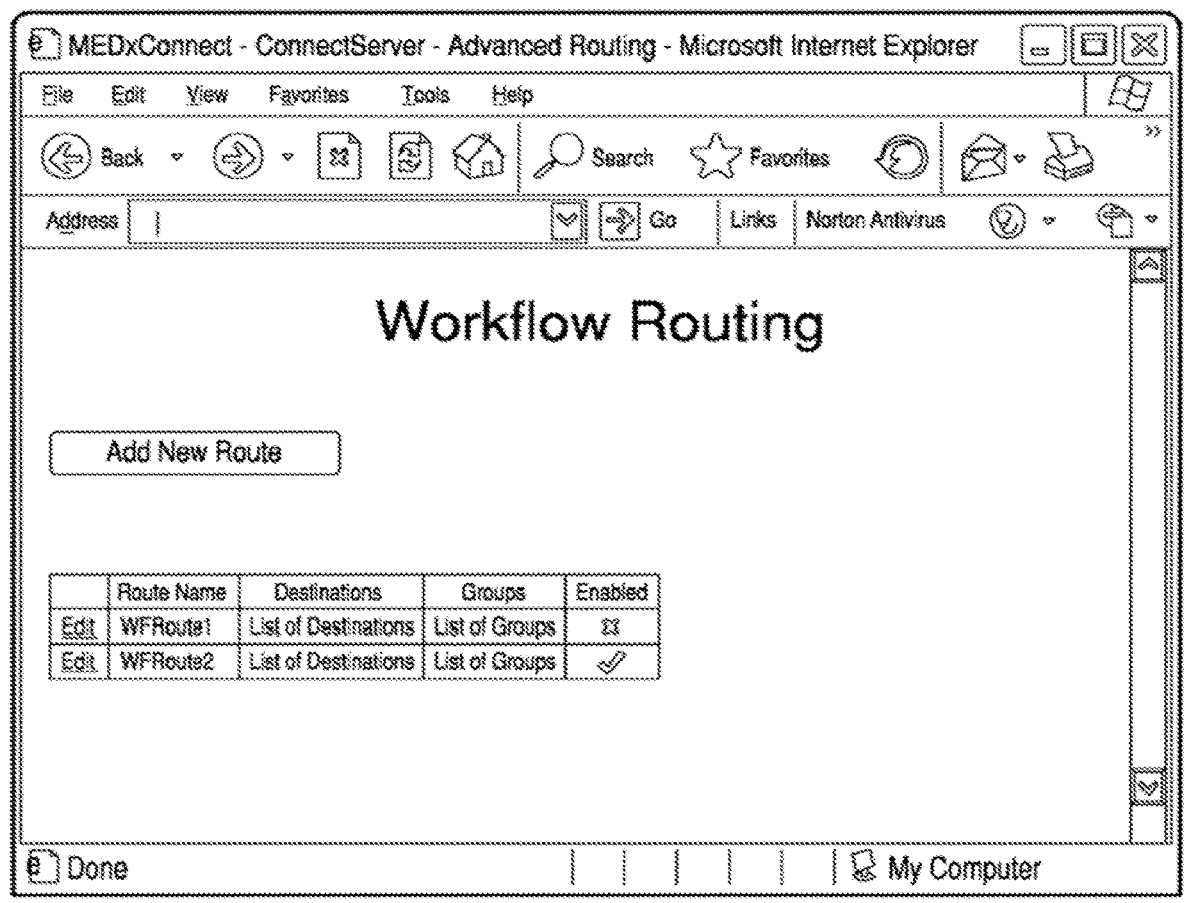

To determine the destination of a study order, the Workflow Manager applies routing rules to the data contents of the study order. The routing rules are customized by an administrator for a particular healthcare enterprise. The rules may be explicitly programmed in a programming language, such as Python, but an embodiment may provide a simpler, table-driven solution for programming the workflow routing rules in the form of a browser-oriented, menu-driven graphical user interface dialog. FIGS. 5a through 5f show an easy-to-use user interface for an embodiment which uses such user inputs to create or update routing rules. The specific selections may be saved as fields in an entry of a routing rule database. Then, whenever a patient study needs to be routed, the routing entries of the routing rule database are each compared with the contents of the study order, the date and time, and the current workflow loads at various destinations. If the criteria of a rule in the routing database are met, then the rule may determine the routing of the study. FIGS. 5a and 5b are simply user interface dialogs to direct an administrator to a browser page like that shown in FIG. 5c, which is continued in FIG. 5d. The interactive browser pages shown in FIGS. 5c and 5d offer the administrator an easy way to create or modify a routing rule. FIG. 5e shows an alternative browser page which offers the user an opportunity to set or edit advanced criteria for time-based rules.

Figure 5C:
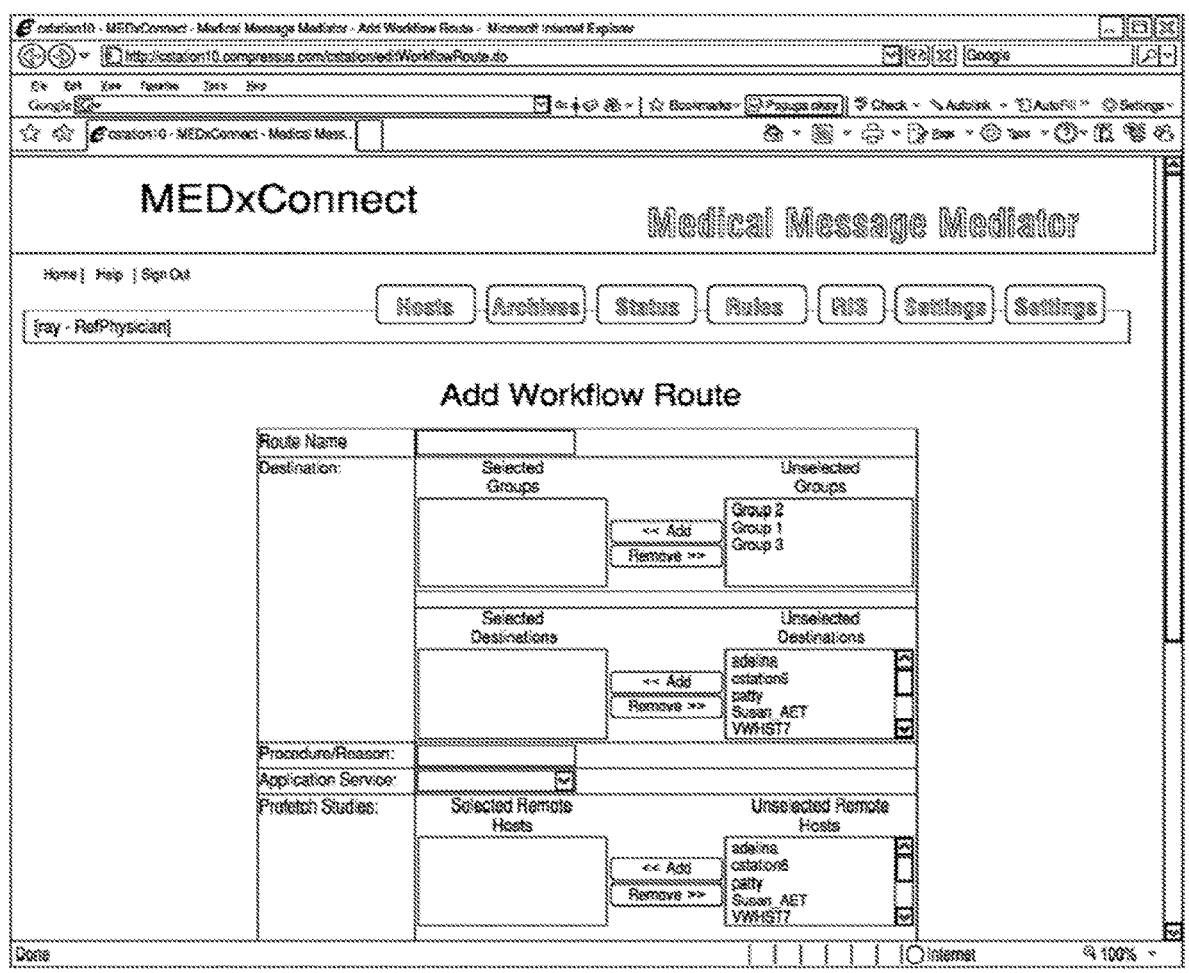
Figure 5D:
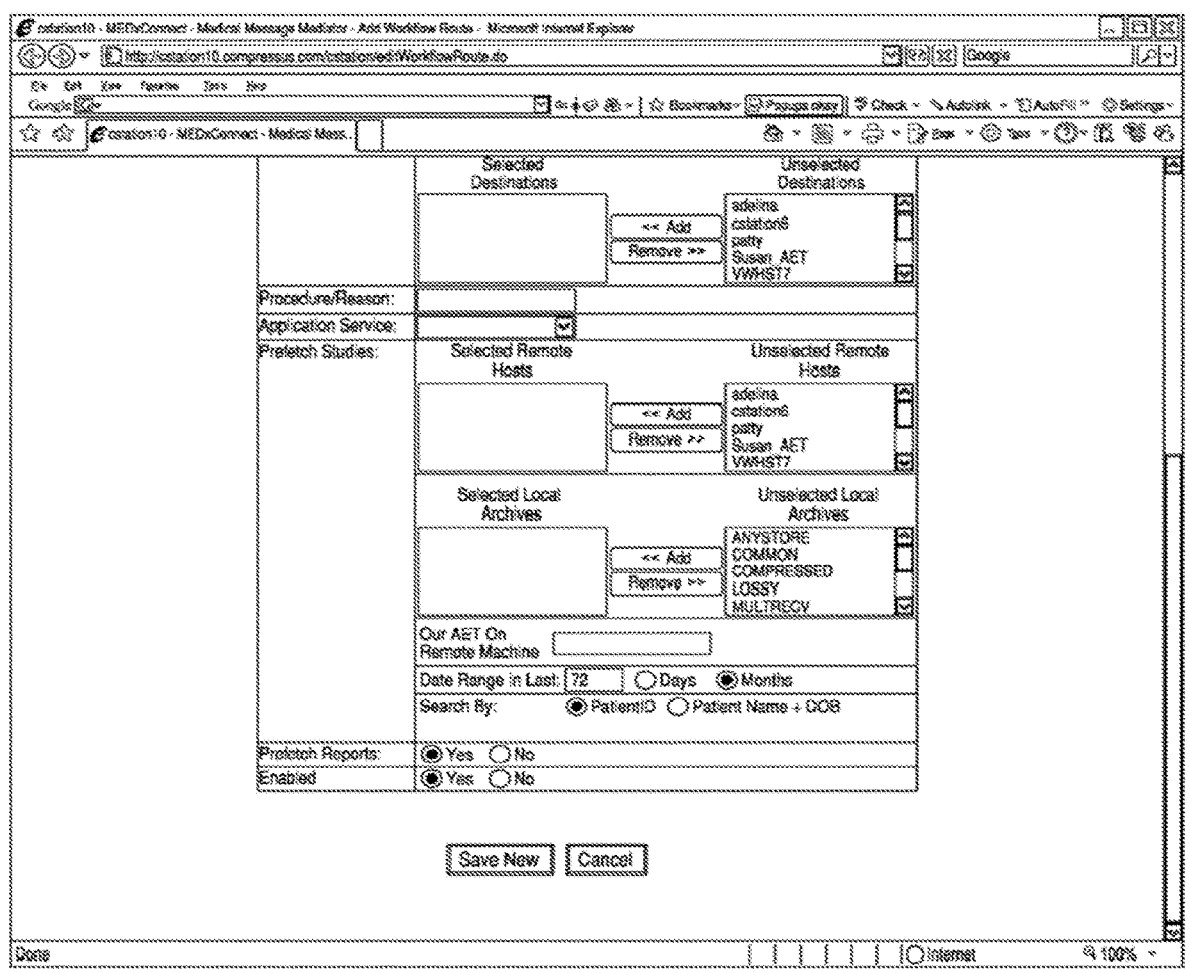
Figure 5E:
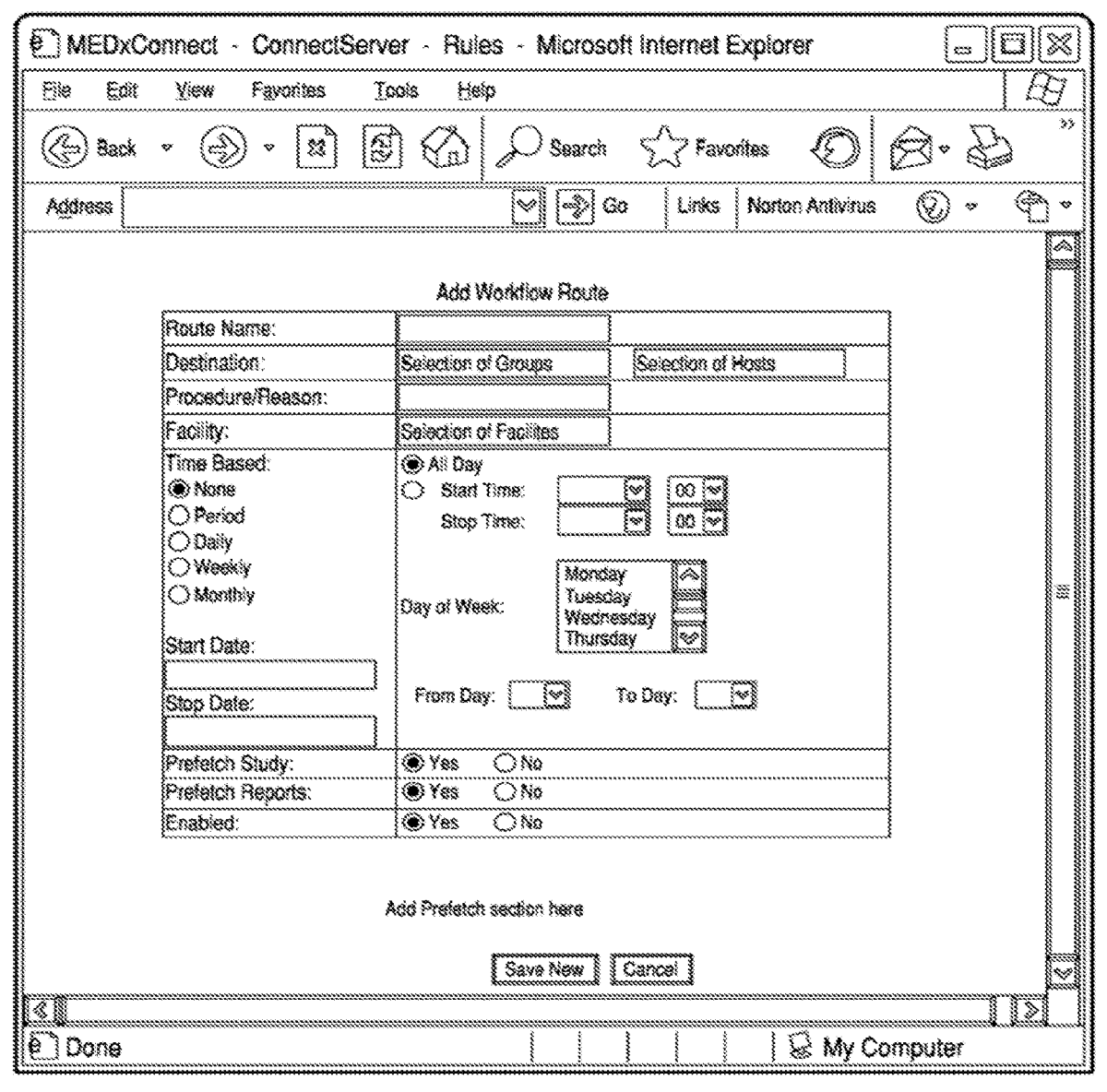
Figure 5F:
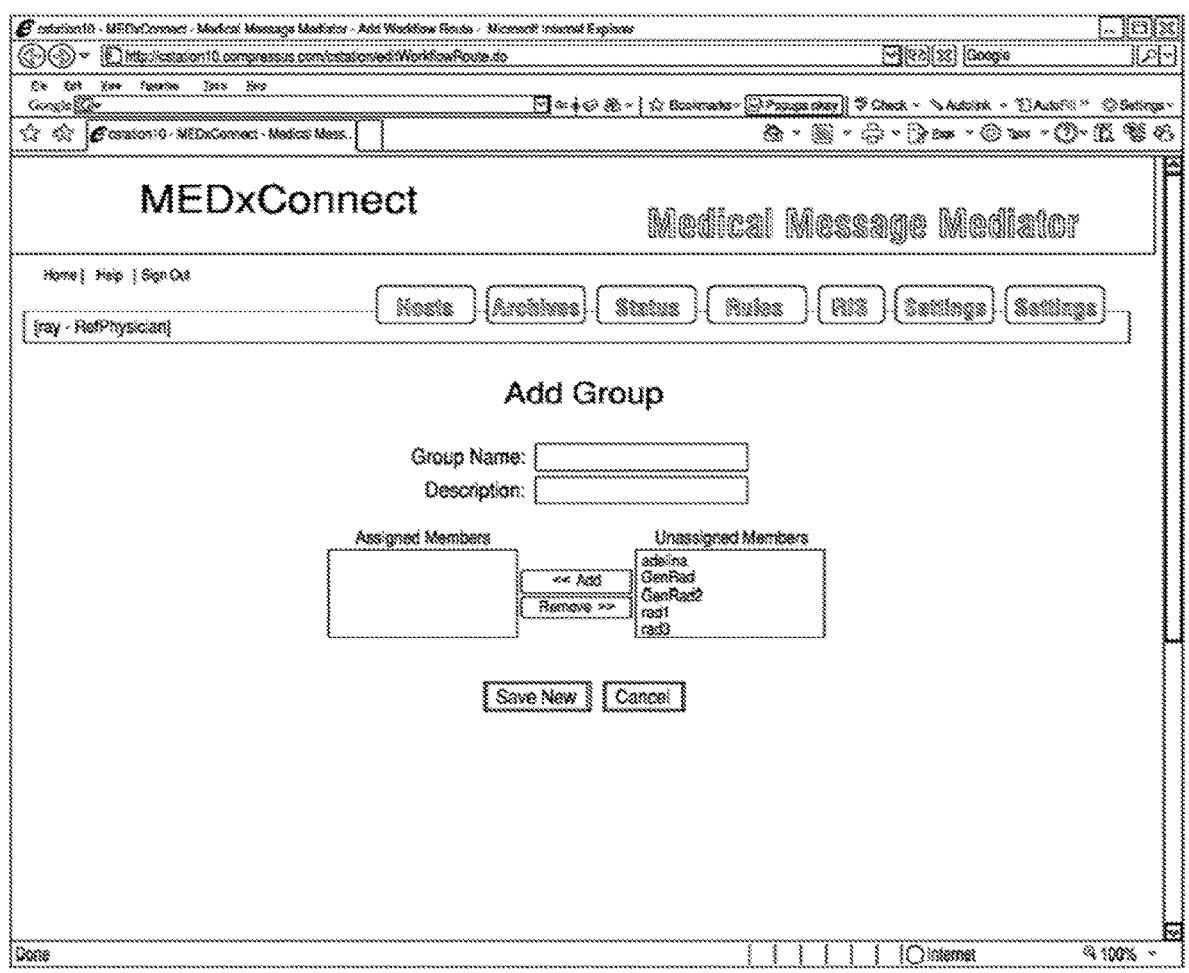

FIG. 5f shows an example dialog menu for defining or modifying a group of physicians that may act as a virtual destination for patient studies.

The automated routing of study orders may be controlled by any of several criteria, a few of which are illustrated in FIGS. 5c through 5e. Routing rules, implemented in modifiable, enterprise-specific, locally-defined tables for example, can automatically route patient studies based on the imaging modality of the ordered study, such as CT, MRI, ultrasound, nuclear medicine, CR, or DR. Routing of study orders can also be based upon a specified body part, such as chest, knee, brain, cervical spine, lumbar spine, etc. In addition, study orders routing can be based on the institution's name or on the referring physician's name that appears in the DICOM tags of the study. Alternatively, study order routing may be based on patient location or patient insurance carrier.

The routing of a study order and the associated studies and reports can also be based on time-based rules. FIG. 5e shows an example of a browser page for creating and updating time-based rules. Time-based rules can be created to route studies according to a specific time range, date, or day of the week. For example, a time-based routing rule could be: "after 7:00 p.m. and before 6:00 a.m. every weekday, route all studies to an offsite reading service or PACS System." Enterprise system information technology (IT) administrators may configure the time-based rules to have the highest precedence, thereby overriding any other rules. This precedence configuration will prevent studies from being forwarded to a diagnostic physician who is at home, on vacation or otherwise unable to complete the report in a timely manner. Of course, low precedence, catch-all, default rules may also be included.

The routing rules may also control the routing of a study based on the current loading of alternative destinations. The number of study orders (the load) listed on the worklist for one destination may be greater than the number of study orders listed on the worklists of other alternative destinations. This may be especially true for healthcare enterprises that have a large number of available diagnosticians or other resources. To help balance workloads, there may be routing rules which depend upon (i.e., conditional rules) on the loads of various alternative destinations. For example, a new study order might be assigned to an alternative destination (i.e., a destination other than what the other routing rules would have selected) with the least load or to any of the alternative destinations for which the load is not already at a programmed maximum value. The maximum value may depend on the number of physicians available at the destination, on the historical responsiveness of the destination, on cost effectiveness of a radiologist or radiology group, on the number of workstations available at the destination, and/or on the throughput of a network link to the destination. Such load-based rules help prevent workflow bottlenecks, balance the system, and thereby improve efficient use of the resources (both workstations and personnel) throughout the healthcare enterprise.

Moreover, routing rules may be customized in order to minimize bottlenecks due to human inefficiency. For example, network bottlenecks may occur as a result of physician, radiologist, or group who is slow to claim healthcare data orders which have been assigned or routed to them. Network bottlenecks may also occur when a physician, radiologist, or group claims an order but is slow to review and provide a study order report. A healthcare enterprise network administrator may set a predetermined limit for the expected elapsed time between when a healthcare data order is claimed and when a report is submitted on that healthcare data order. Routing rules may be automatically customized to limit the number of healthcare data orders assigned or routed to a physician, radiologist or group who record an elapsed time which exceeds the predetermined limit. Elapsed times may be recorded in the memory of the workstation/server unit accessed by the physician, radiologist or group. The recorded elapsed times can be accessed and utilized by either network monitoring software or to routing rules software to allow for automatic customization of routing rules.

In order to improve efficiency, the system can collect historical diagnostic throughput information, which may be logged into a transaction journal. The transactions, for example, may be time-stamped and sorted according to destination groups and each group rated according to elapsed time or expense of diagnostic throughput, for example. Throughput may be measured as the time between when a study order originates and when the report on the study is completed and routed to its final destination. Such information may be used by an administrator to adjust the routing rules.

The routing table may be administered from a Web-based management console. Such a console permits the system administrator to create rules based upon required workload and resource availability for an administrator log-in. Existing DICOM or XML tagged data may trigger rules in a hierarchical order. The rules may be implemented in a table of routing parameters, such as illustrated in FIG. 6c, or in some high level programming language. An interpreted, network browser-friendly language such as Java, Perl, Python, or Ruby may allow for easier, more dynamic, on-the-fly updates than a compiled language like C or C++.

FIGS. 6a through 6j show the data fields of example record structures which may be used to implement an embodiment. Descriptions of the fields are included in the figures, and the field names are self-descriptive. FIGS. 6a and 6b describe records to define a particular entry in the routing table and a routing destination group. These records can store the data entered in the user interface dialogs shown in FIGS. 5c, 5d, and 5e. FIG. 6c shows example data field parameters of a workflow routing rule table for an example routing rule database, which is similar to FIG. 6a but allows storage of the text of a programmed routing criterion in field Rule. FIGS. 6d, 6e, and 6f show example data structures which an embodiment can use to track the transmission and reception of the images related to a specific study order. FIGS. 6g and 6h show example data structures that can be used to keep track of the transmission of various pre-fetched images to be presented to a diagnostician claiming a study order at a workstation. FIGS. 6i and 6j show example data structures of records which track the status of the transmission of a study consisting of the set of images of the patient of a study order.

Other database tables may be used, such as a Workflow Package table which lists the accession numbers of existing study orders and their images. To verify if an image is a workflow image, the StuInsUID field value of the Received-Images table is used to query the Workflow Package table for the accession number of the study that the image is a part of. If no table entry exists, the new image is not a workflow image. Further, a Workflow table maintains the current Status of each active order.

Figure 7:
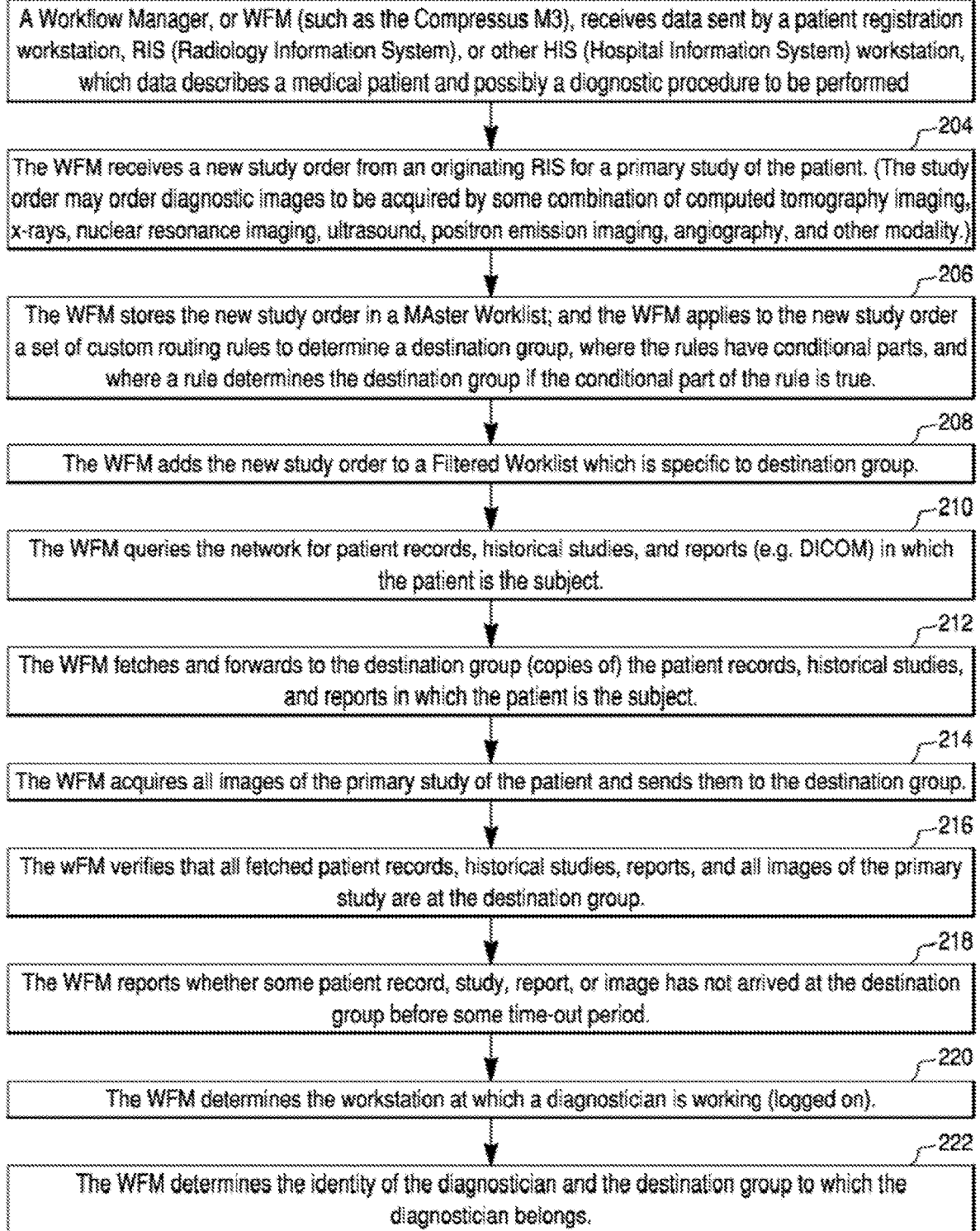
FIG. 7 lists actions which a Workflow Manager may perform to manage the workflow processing of studies.
Figure 7:
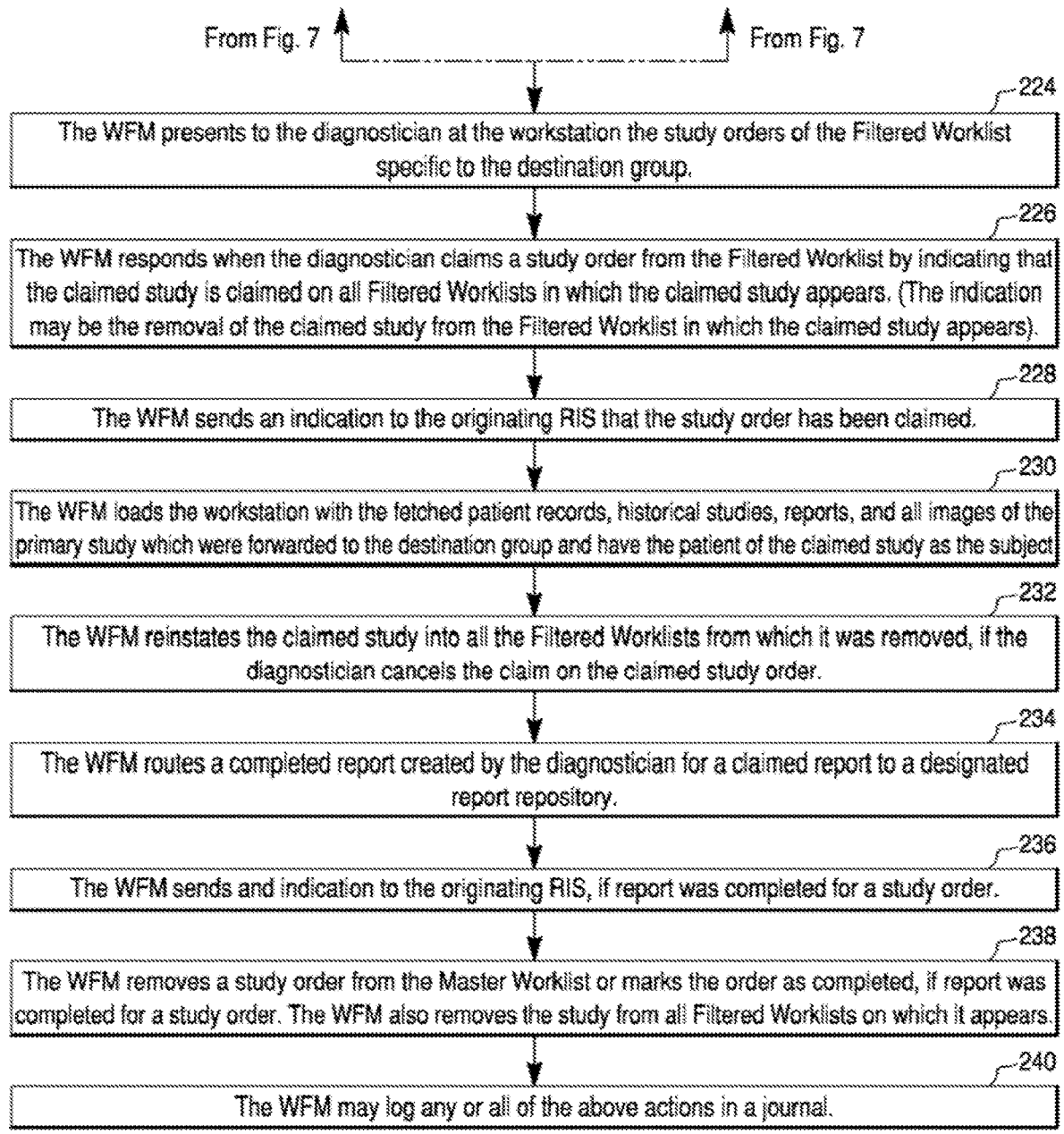

FIG. 7 lists method steps which a Workflow Manager of an embodiment may perform to automate and manage workflow for medical image retrieval, display, and analysis on a network. Referring to FIG. 7, the Workflow Manager (WFM) may receive patient data from an HIS or RIS patient registration workstation, step 202. The patient data may include demographic information, details about a scheduled procedure, the name of a referring physician, and the like. Some of the data, such as the patient's demographic data, may already be available within a database accessible within the enterprise network.

The same workstation or a different one may be used to originate a new imaging study, such as by means of a new study order in the form of a HL7/ORM message, step 204. The study order may be in the format of an entry in DICOM modality worklist. The new study order may include information about the imaging modality (X-ray, CT, MRI, ultrasound, PET, angiography, etc.). The study order may name the anatomy to be imaged (knee, hip, or chest for example), a procedure code, and so forth. The study order is sent to the Workflow Manager from the originating imaging system, that is, from the workstation of the imaging system. The Workflow Manager receives the study order in step 204. The sending of a new study order to the Workflow Manager may be automatically initiated, for example, when a Workflow Manager client on an imaging workstation somewhere on the network detects the action of locally generating a new study order.

After the Workflow Manager receives the new study order, the Workflow Manager applies the routing rules to the study order to determine which group (or groups) is the destination for the study order, step 206. Further details of applying routing rules will be provided subsequently. Workflow Manager stores (adds) the order into the Master Worklist as an uncompleted study order, step 206. The members of the destination group may include one or more radiologists, diagnosticians, specialists, or other physicians. The Workflow Manager adds the new study order to the Filtered Worklist specific to the destination group, step 208. The order may be added to the Filtered Worklists of other destination groups as well.

The Workflow Manager queries the network for patient records, archived historical studies and reports, and any other information about the patient that is the subject of the newly ordered study, step 210. In response to the results of the query, the Workflow Manager locates, fetches, compresses, packages, reformats as necessary, and forwards the records, archived studies and reports, and other information to a designated memory (such as a file server) for the destination group, step 212. The designated memory may be a physical or logical network location (e.g., hard disc storage unit coupled to a network server) from which the studies, reports, and other information related to the study order may be efficiently accessed. For example, if a designated group is more likely to log on to a workstation at a remote facility, the designated location may be a network file server or a workstation at that remote facility. As another example, the archive from which a historical study or report is fetched may have a slow access time and so may be pre-fetched and copied to the designated location. An example of a slow-access archive is an external medium (like an optical disk or a physical X-ray film) which must be manually located and mounted onto a network accessible drive or scanner.

The Workflow Manager also acquires, compresses, packages, reformats as necessary, and forwards the images taken for the primary study, which is the main objective of the study order itself, step 214. The Workflow Manager may verify that all the primary study images, the archived studies, archived reports, and other files are available and were transferred to the designated memory for the destination group, step 216. If any expected records, studies, images, or other information are missing or unavailable, such as for example after a time-out period, the Workflow Manager may report the problem, step 218. For instance, a DICOM archive may be off-line for maintenance at the time it is queried by the Workflow Manager. An acquisition or transmission problem may be reported to the administrator or in an annotation within the study order. With or without a problem, the study order in the Master Worklist may be changed to a ready-to-read state when all available studies, reports, and patient information are accessible at the designated memory.

When a diagnostician logs in on a diagnostic workstation, the Workflow Manager determines which workstation is being used and determines the identity of the diagnostician, steps 220 and 222. In an embodiment, the diagnostician can perform all analysis during a single login session on any diagnostic workstation on the network. A diagnostic workstation may include a personal computer connected to the enterprise network or a workstation associated with an imaging system. Knowing the specific workstation and the identity of the diagnostician, the Workflow Manager can present the Filtered Worklist specific to the group to which the diagnostician belongs, step 224. The Filtered Worklist (i.e., the list of unclaimed study orders in the Filtered Worklist) may be displayed on the workstation by a local client component of the Workflow Manager, by a Java applet, by a Web browser, or any other display software or component. The local client component may operate in cooperation with a server component of the Workflow Manager, which may be executing on a server somewhere else on the network. An optional but attractive feature of the displayed form of the Filtered Worklist is the ability to sort the displayed list of study orders by some criterion. The criterion may be the name of the patient, the modality, the date of the study, or some other data field of the study order.

The logged-in diagnostician can claim a study order from the displayed Filtered Worklist through the graphical user interface of the workstation, step 226. A particular study order in the displayed Filtered Worklist may be selected and claimed by means of conventional keyboard, touch screen, light pen or mouse input. For example, the diagnostician may highlight the representation of the particular study on the workstation screen and click the mouse cursor on a screen button labeled "Claim." The Workflow Manager then indicates that this newly claimed study is now claimed on all Filtered Worklists on the network in which the claimed study appears. For example, a second diagnostician of the same destination group may also be logged in (on a different workstation) and viewing his or her own display of the same Filtered Worklist. The Workflow Manager insures that the currently claimed study order cannot be simultaneously claimed by the second diagnostician. This feature prevents the two diagnosticians from analyzing the same imaging study, which would be a waste of resources. The claim on a study order in each Filtered Worklist may be indicated by visually marking or by changing the color of the displayed order. Alternatively, the claimed study may simply be removed from the display of all (displayed) Filtered Worklists in which the claimed study appears. The Workflow Manager may optionally send an informational indication to the originating RIS that the study order has been claimed in order to indicate the progress of the study order, step 228. The optional indication may be used to synchronize the state of the study order on the originating RIS, the Master Worklist, and the Filtered Worklist.

At some point a procedure may have been performed, which is the reason that the study order was originally initiated. For the present description, the procedure may be a new, "primary" imaging study including at least one image acquired by an imaging system of some modality. The primary study itself may have been performed before, during, or after the associated study order is sent to the Workflow Manager. At some time before the diagnostician is ready to analyze the image or images of the primary study, the Workflow Manager makes at least one image of the primary study accessible to the workstation in use by the diagnostician, step 230. Other historical studies, images, reports, records, and other information related to the same patient may also be fetched ("pre-fetched") from some image source or database on the network and made readily accessible to the workstation. The image source may be an imaging system, a HIS or RIS workstation, a PACS or DICOM archive, a proprietary archive, a network file server, etc. The images, reports, and records may be downloaded directly to the workstation's local memory or they may be moved to a server having a fast communication link to the workstation. Accessibility of the images, studies, and information may include automatically compressing and/or translating (reformatting) them from one format to a different format which the workstation can display.

If the logged-in diagnostician cancels the claim on the study order, the Workflow Manager reinstates the study order to the unclaimed state in the Filtered Worklist from which it came, step 232. This reverses the action of step 226 and normally would occur, if at all, before the diagnostician generates a report. The Workflow Manager indicates that the reinstated study order may subsequently be claimed by another member of the destination group. The Workflow Manager may indicate that the order is reinstated by insuring that the order reappears on all workstations displaying the Filtered Worklist.

The last action of the diagnostician is to create a report on the study. The report may be a verbal dictation, a typed textual message, or some other form acceptable to the enterprise. The final step for the Workflow Manager is to route the completed report to a designated repository, step 234. This can happen while the study order is claimed by the logged-in diagnostician.

The Workflow Manager may need to perform some wrap-up actions which synchronize the state of the study order in the originating (RIS) imaging system, the Master Worklist, and the Filtered Worklist. The Workflow Manager sends a completion indication to the RIS system or imaging workstation which originated the study order, step 236. The Workflow Manager removes the study order from all Filtered Worklists on which the study order appears, step 238. The Workflow Manager also marks the study order as complete in the Master Worklist, step 238. This may involve the removal of the study order from the Master Worklist.

An embodiment may further log any or all of the above actions in a journal, together with timestamps, for further scrutiny by an administrator in order to customize the routing rules and improve image analysis throughput Improving the throughput may be defined, for example, as minimizing the average elapsed time between receiving the study order from the imaging workstation and routing the report.

In an embodiment, the routing rules can be customized to minimize the average cost of the time expended by the logged-in diagnostician between when the logged-in diagnostician claims the study order and when the routing of the report occurs. Statistics like the average cost may be computed by analyzing the execution times of the time-stamped actions logged into the journal times an average cost per unit time value for the diagnostician, group, or workstation. The analysis can be directed to the average network delivery times, the average computer processing times, or the average elapsed analysis times (and hourly costs) of the human diagnosticians. These times can be reviewed by an administrator to identify the recurring hardware, software, and human bottlenecks in system workload.

Figure 8A:
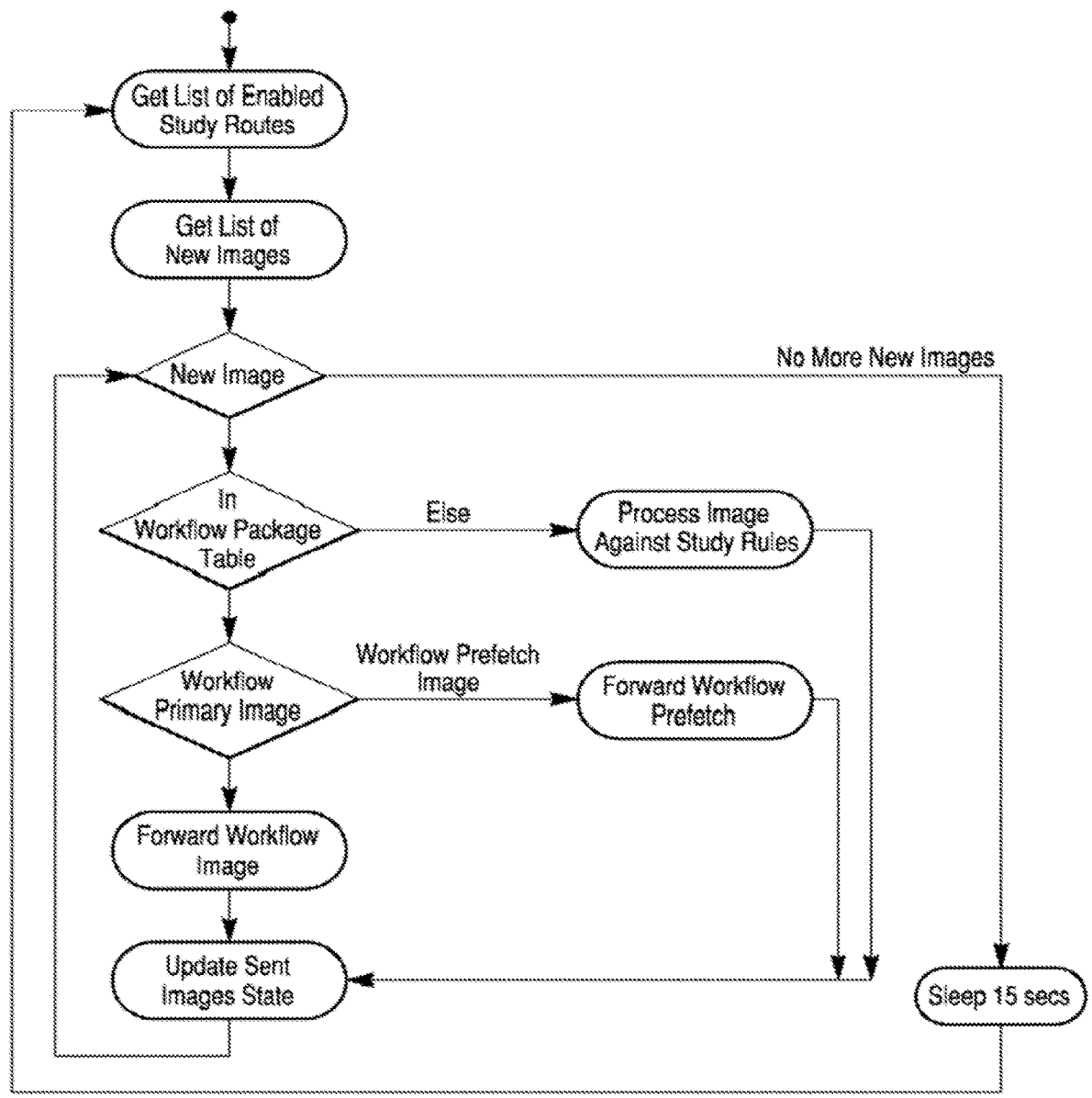

FIGS. 8a through 11 are flowcharts and equivalent pseudo-code giving more details of how the Workflow Manager may apply the routing rules in step 206 of FIG. 7 to a new study. FIGS. 8a and 8b describe the evaluation of new images that may be part of a study to determine the disposition of the images according to the study routing rules. The process of FIG. 8a checks the ReceivedImages table (see FIG. 6e) for any new images received. A new image may be evaluated against the Study Routing rules and queued in the SentImages table appropriately.

Figure 9A:
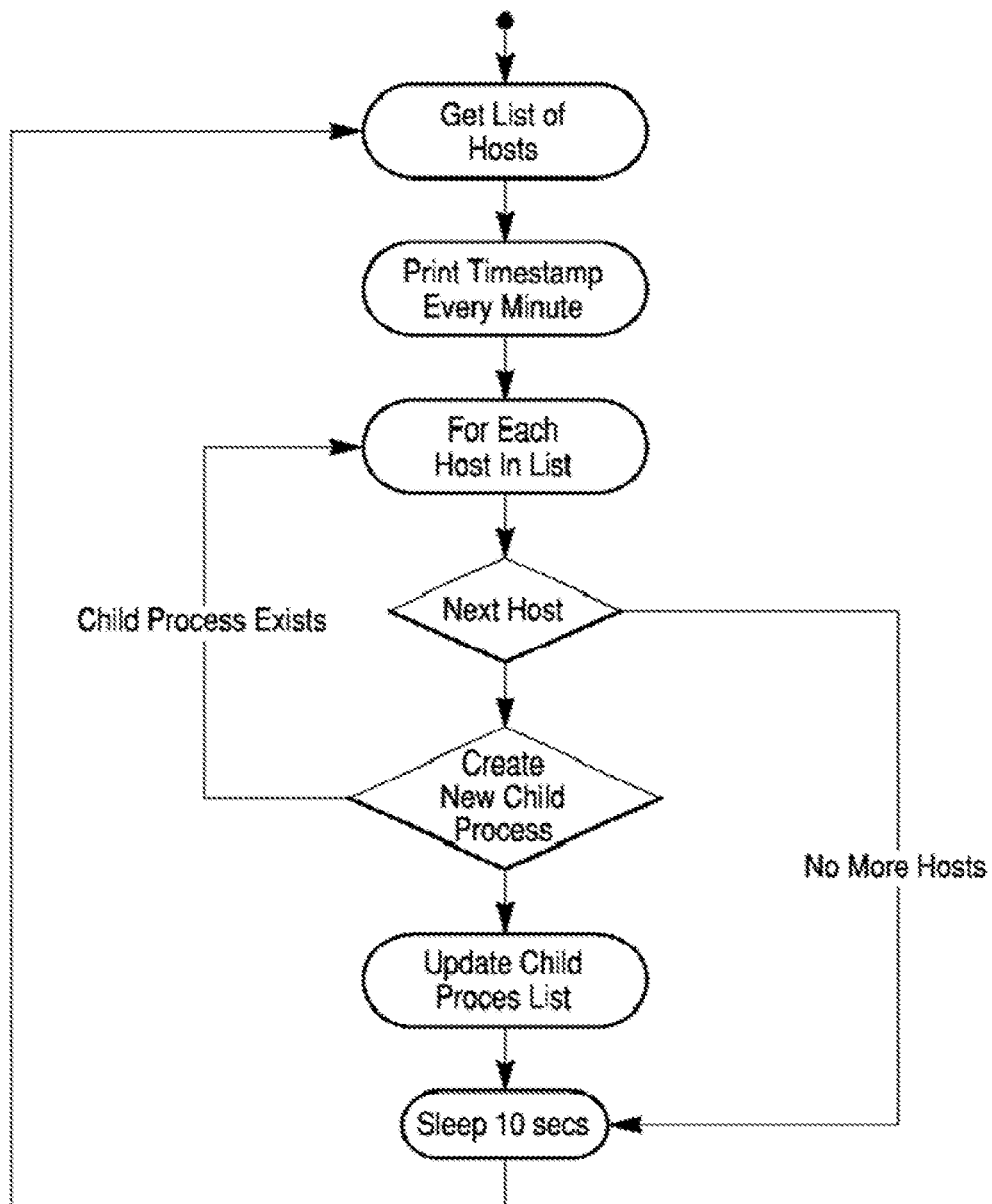
Figure 9C:
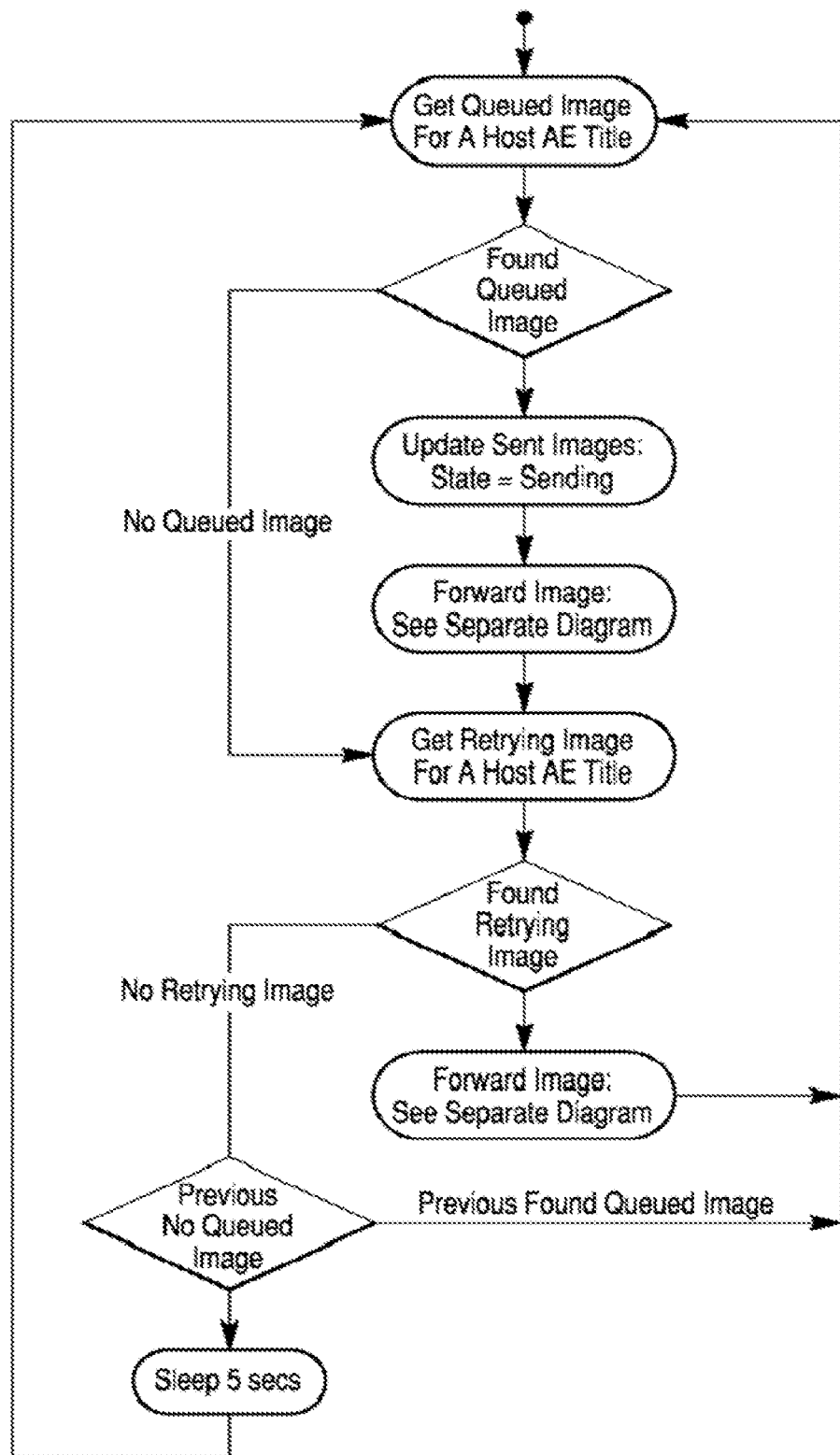
Figure 9D:
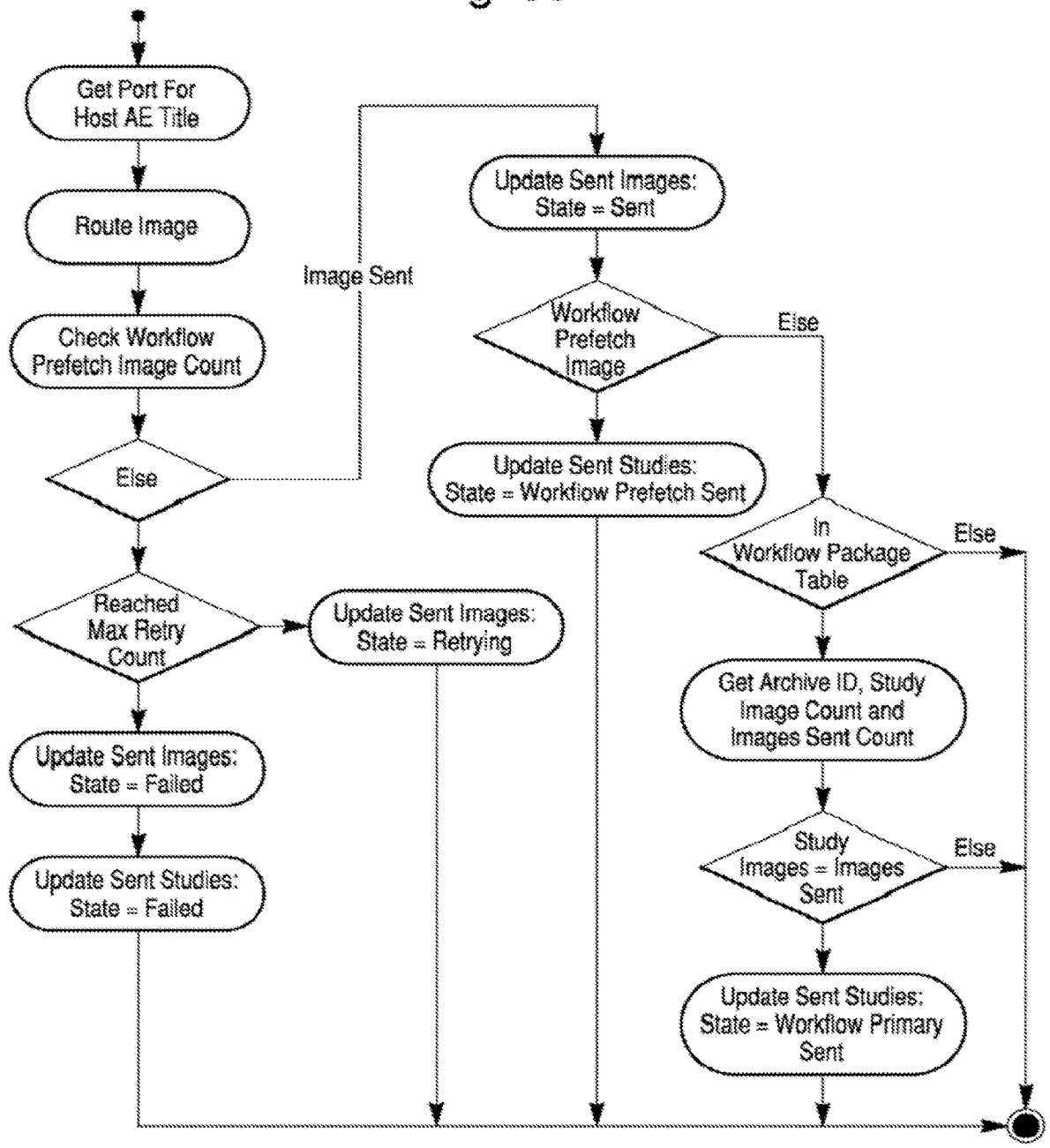

For the new workflow image, the AccessionNo is used to check if the image is part of a study order. If so, the AccessionDest table is queried by the AccessionNo to determine which destinations/groups in which to route the workflow image. If the FirstSentTS has not been updated for the rows with that AccessionNo, all are updated with the current timestamp as the first workflow image for that study has now been received. Then, for each unique destination found, the image is queued in the SentImages table to be routed by the cstation_routerimages process (FIG. 9a).

FIGS. 9a through 9e provide flowcharts and pseudo-code for a detailed example for cstation_routerimages process. The cstation_routerimages process is responsible for routing State="Queued" images in the SentImages table. If the cstation_routerimages process does not succeed in sending an image the first time the process sees the image, the process retries to send the image 5 times before the process sets the image State as "Failed." Once an image has been sent, the process checks to see if the image is the last one in a study to be routed and updates the SentStudies table appropriately.

On startup, the main cstation_routerimages process queries the SentImages table for images with the State="Sending." It updates each image to State="Queued" to resend them before starting the child router processes. Images may be caught in this intermediate State if the cstation_routerimages process is restarted or rebooted when the process is in the middle of sending an image. To make sure that the image(s) is resent, the image State is set to "Queued" to be sent again.

Figure 10:
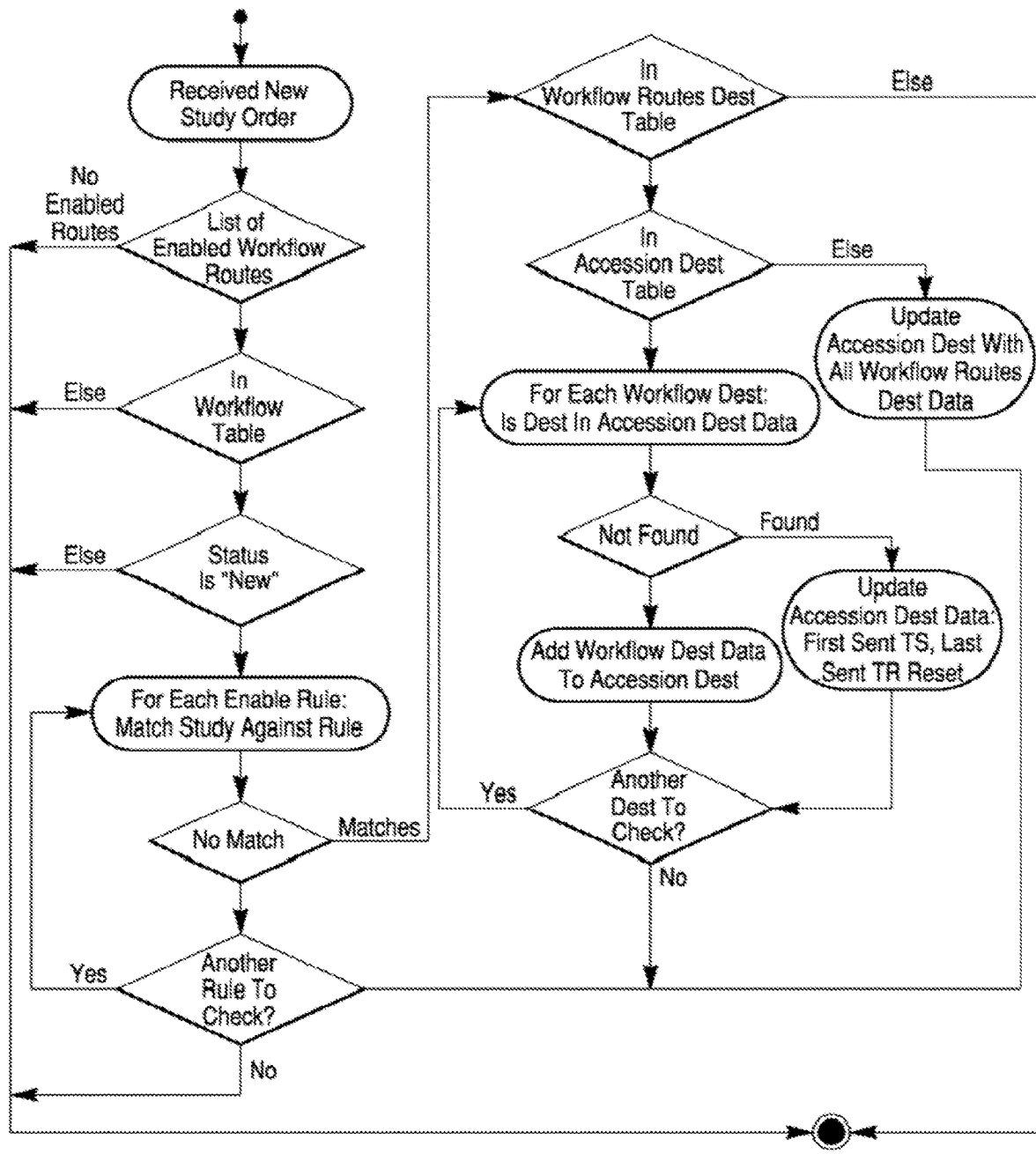

FIG. 10 provides a flowchart for the EvalWorkflowRules function. The Workflow Manager calls this function to evaluate a newly ordered study against the enabled workflow routing rules. The accession number of the study is passed in to the function. For each workflow routing rule that the new order satisfies, an entry in the AccessionDest table is added for each group and/or host destination associated with that rule. If data already exists in the AccessionDest table, the FirstSentTS and LastSentTS fields are updated to 0.

Figure 11:
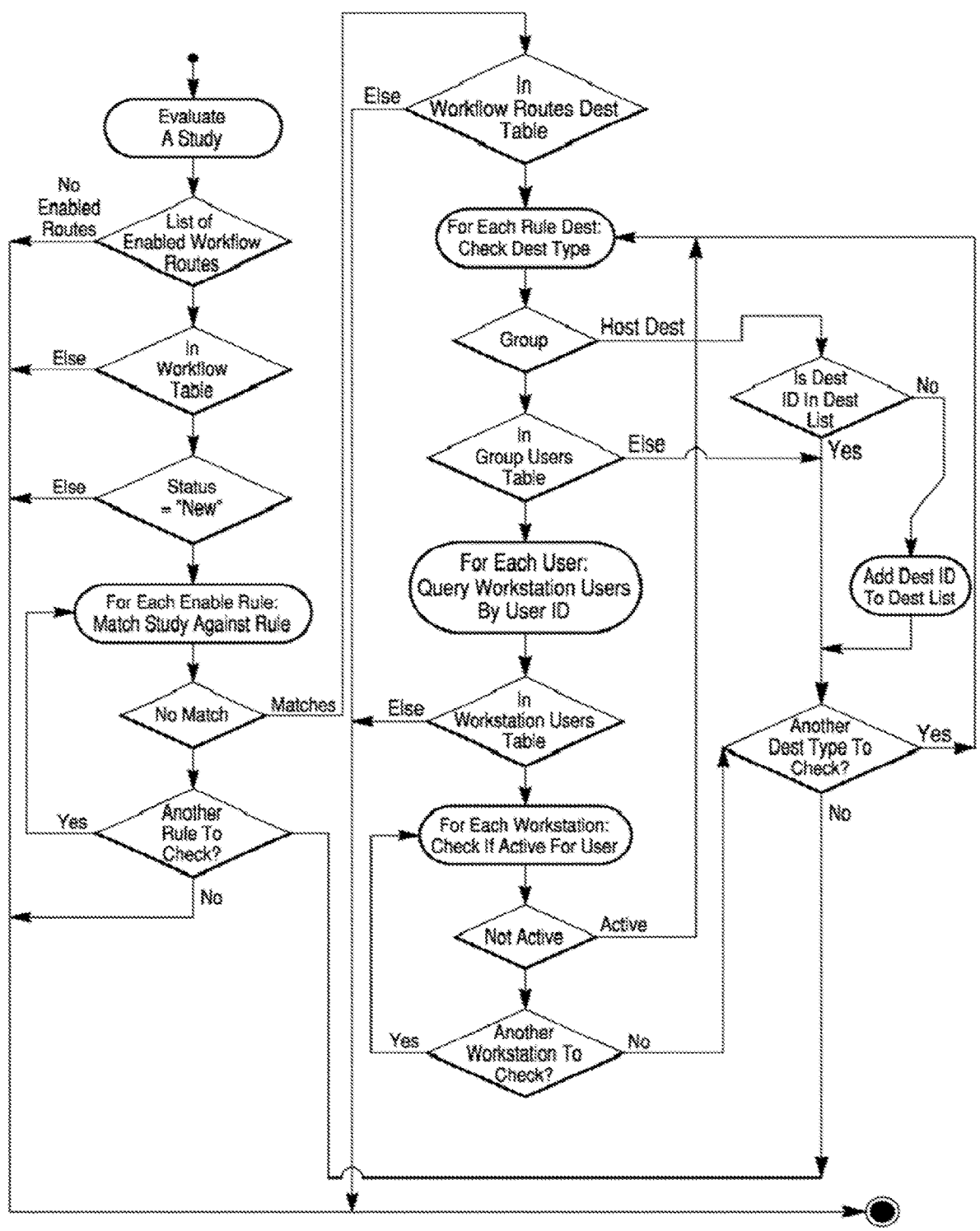

FIG. 11 provides a flowchart for the GetEvalWorkflowDestList function. This function evaluates the specified study against the enabled workflow routing rules and returns a list of destination Ids to which to route the study. The accession number of the study is passed in to the function.

While the present invention has been disclosed with reference to certain example embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

We claim:

1. A method comprising:
automating and managing workflow for healthcare data retrieval, display, and analysis on a healthcare enterprise network and establishing interoperability between nodes of the healthcare enterprise network, wherein the automating and managing workflow and establishing the interoperability between nodes of the healthcare network comprise:
receiving a study order for a patient from a first workstation of an imaging system on the healthcare enterprise network, wherein the study order contains data associated with at least one study image;
storing the study order in a master worklist on a network server as an uncompleted study order;
collecting and organizing network locations of data related to a patient in an enterprise-wide database using interrelated data structures in a computer memory to store the data related to the patient so that programmed rules provided to a workflow manager can test the contents of the various fields of the data structures to determine a destination group of a study order in the worklist;
testing the contents of the various fields of the data structures to determine the destination group of a study order;
applying a workflow routing rule to data associated with the at least one study image contained in the study order to a route the workflow to determine the destination group, wherein the workflow routing rule depends on at least one of a criticality of the study order, image modality, and a body part in the at least one study image, the routing rules are implemented in enterprise-specific, locally-defined tables that are utilized to automatically route patient studies based on an at least imaging property of the study order, the routing rules comprise conditional rules that depend upon on loads and responsiveness of destinations to facilitate balancing routing workloads;
adding the study order to a first filtered worklist which is specific to the destination group;
acquiring study order related data from the nodes of the healthcare enterprise network, wherein sets of the study order related data have differing formats;
manipulating file characteristics of the data including compiling the data from a variety of differing formats on a number of workstations into a common format, to render the data accessible by a workstation of the destination group to establish the interoperability between the nodes of the healthcare enterprise network;
storing information related to the study order in a designated memory associated with the destination group;
displaying the first filtered worklist on a second workstation in use by a logged-in user who is a member of the destination group;
making accessible to the second workstation an image of the primary study of the patient associated with the study order;
accepting a claim of the study order from the logged in user;
preventing the claimed study order from being claimed by any other user;

receiving a report created by the logged-in user;

routing the report, in accordance with the modifiable, enterprise-specific, locally-defined tables, to a designated repository while the study order is claimed by the logged-in user;

removing the study order from the first filtered worklist from any other filtered worklist on which the study order appears;

sending an indication to the first workstation that the study order has been completed;

marking the study order in the master worklist as complete;

updating historical diagnostic throughput information based on a measured diagnostic throughput of the study, wherein the measured diagnostic throughput comprises an elapsed amount of time or expense between receiving the study order and marking the study order as complete; and adjusting the workflow routing rule base on the updated historical diagnostic throughput information.

2. The method of claim 1, wherein the first workstation and the second workstation are the same.

3. The method of claim 2, further comprising automatically translating patient images and demographic data from a first diagnostic image format to a second diagnostic image format.

4. The method of claim 1, further comprising: accepting a cancellation of the claim of the study order from the logged in user; and indicating that the study order may be claimed by another member of the destination group when the logged-in user cancels the claim on the study order.

5. The method of claim 4, wherein indicating that the study order may be claimed is achieved by including the study order in the first filtered worklist.

6. The method of claim 1, further comprising: synchronizing study orders on workstations connected to the healthcare enterprise network, study orders included in the master worklist, and study orders included in the first filtered worklist.

7. The method of claim 1, wherein preventing the claimed study order from being claimed by any other user is accomplished by removing the claimed study order from every filtered worklist in which the claimed study order appears.

8. The method of claim 1, further comprising maintaining a status of the study order in the master worklist such that the study order can be claimed by only one user at a time.

9. The method of claim 1, wherein the destination group is a group of one or more physicians.

10. The method of claim 1, wherein the study order is in a DICOM modality worklist.

11. The method of claim 1, further comprising: detecting a new study order received somewhere on the healthcare enterprise network; and adding the new study order to the master worklist.

12. The method of claim 1, further comprising sorting a sequence of the study orders of the filtered worklist displayed on the second workstation.

13. The method of claim 1, further comprising storing an elapsed time between when the study order is claimed and when the report is received.

14. The method of claim 1, further comprising prefetching diagnostic images from DICOM archives.

15. The method of claim 1, wherein the workflow routing rule further depends on at least one of a name of a referring physician of a diagnostic image, a name of a diagnostic physician, a patient location, a patient insurance carrier, a time range, a date range, and specific days of the week.

16. The method of claim 1, wherein marking the study order in the master worklist as complete is achieved by removing the study order from the master worklist.

17. The method of claim 1, wherein the study order related data includes one or more of: historical studies, patient records, and reports related to the study order.

18. The method of claim 1, wherein the user comprises a diagnostician.

* * * * *